US008105771B2

(12) United States Patent
Drmanac

(10) Patent No.: US 8,105,771 B2
(45) Date of Patent: *Jan. 31, 2012

(54) RANDOM ARRAY DNA ANALYSIS BY HYBRIDIZATION

(75) Inventor: Radoje T. Drmanac, Los Altos Hills, CA (US)

(73) Assignee: Callida Genomics, Inc., Sunnyvale, CA (US)

( * ) Notice: Subject to any disclaimer, the term of this patent is extended or adjusted under 35 U.S.C. 154(b) by 587 days.

This patent is subject to a terminal disclaimer.

(21) Appl. No.: 10/547,214

(22) PCT Filed: Feb. 26, 2004

(86) PCT No.: PCT/US2004/006022
§ 371 (c)(1),
(2), (4) Date: Jun. 29, 2006

(87) PCT Pub. No.: WO2004/076683
PCT Pub. Date: Sep. 10, 2004

(65) Prior Publication Data
US 2007/0037152 A1 Feb. 15, 2007

Related U.S. Application Data

(60) Provisional application No. 60/450,566, filed on Feb. 26, 2003.

(51) Int. Cl.
*C12Q 1/68* (2006.01)
*C12P 19/34* (2006.01)
(52) U.S. Cl. ................ 435/6.1; 435/6.11; 435/6.12
(58) Field of Classification Search ............... None
See application file for complete search history.

(56) References Cited

U.S. PATENT DOCUMENTS

| | | |
|---|---|---|
| 4,719,179 A | 1/1988 | Baranay |
| 4,883,750 A | 11/1989 | Whiteley |
| 5,091,302 A | 2/1992 | Newman et al. |
| 5,124,246 A | 6/1992 | Urdea |
| 5,143,854 A | 9/1992 | Pirrung |
| 5,202,231 A | 4/1993 | Drmanac et al. |
| 5,403,708 A | 4/1995 | Brennan |
| 5,427,930 A | 6/1995 | Birkenmeyer |
| 5,474,796 A | 12/1995 | Brennan |
| 5,508,169 A | 4/1996 | Deugau |
| 5,525,464 A | 6/1996 | Drmanac et al. |
| 5,632,957 A | 5/1997 | Heller et al. |
| 5,641,658 A | 6/1997 | Adams |
| 5,700,637 A | 12/1997 | Southern |
| 5,728,524 A | 3/1998 | Sibson |
| 5,744,305 A | 4/1998 | Fodor |
| 5,800,992 A | 9/1998 | Fodor |
| 5,866,337 A | 2/1999 | Schon |
| 5,871,921 A | 2/1999 | Landegren |
| 5,888,737 A | 3/1999 | DuBridge |
| 6,004,755 A | 12/1999 | Wang |
| 6,013,445 A | 1/2000 | Albrecht |
| 6,045,994 A | 4/2000 | Zabeau |
| 6,124,120 A | 9/2000 | Lizardi |
| 6,136,537 A | 10/2000 | Macevicz |
| 6,143,495 A | 11/2000 | Lizardi |
| 6,143,527 A | 11/2000 | Pachuk |
| 6,210,891 B1 | 4/2001 | Nyren |
| 6,210,894 B1 | 4/2001 | Brennan |
| 6,251,639 B1 | 6/2001 | Kurn |
| 6,255,469 B1 | 7/2001 | Seeman |
| 6,258,539 B1 | 7/2001 | Hunkapillar |
| 6,270,961 B1 | 8/2001 | Drmanac |
| 6,291,183 B1 | 9/2001 | Pirrung |
| 6,297,006 B1 | 10/2001 | Drmanac |
| 6,297,016 B1 | 10/2001 | Egholm |
| 6,306,597 B1 | 10/2001 | Macevicz |
| 6,309,824 B1 | 10/2001 | Drmanac |
| 6,316,229 B1 | 11/2001 | Lizardi |
| 6,329,150 B1 | 12/2001 | Lizardi |
| 6,346,413 B1 | 2/2002 | Fodor |
| 6,355,419 B1 | 3/2002 | Alfenito |
| 6,355,432 B1 | 3/2002 | Fodor |
| 6,401,267 B1 | 6/2002 | Drmanac |
| 6,403,320 B1 | 6/2002 | Read |
| 6,413,722 B1 | 7/2002 | Arnold |
| 6,432,360 B1 | 8/2002 | Church |
| 6,472,156 B1 | 10/2002 | Wittwer et al. |
| 6,491,871 B1 | 12/2002 | Fodor |
| 6,500,620 B2 | 12/2002 | Yu |
| 6,506,594 B1 * | 1/2003 | Barany et al. ............ 435/287.2 |
| 6,514,768 B1 | 2/2003 | Guire |
| 6,534,293 B1 | 3/2003 | Baranay |
| 6,573,369 B2 | 6/2003 | Henderson |
| 6,589,726 B1 | 7/2003 | Butler |
| 6,620,584 B1 | 9/2003 | Chee |
| 6,653,077 B1 | 11/2003 | Brenner |
| 6,787,308 B2 | 9/2004 | Balasubramanian |
| 6,812,005 B2 | 11/2004 | Fan |
| 6,828,100 B1 | 12/2004 | Ronaghi |
| 6,833,246 B2 | 12/2004 | Balasubramanian |
| 6,864,052 B1 | 3/2005 | Drmanac |
| 6,890,741 B2 | 5/2005 | Fan |
| 6,913,884 B2 * | 7/2005 | Stuelpnagel et al. ............ 435/6 |
| 6,998,228 B2 | 2/2006 | Henderson |
| 7,011,945 B2 | 3/2006 | Qiao |

(Continued)

FOREIGN PATENT DOCUMENTS

JP 4-262799 9/1992

(Continued)

OTHER PUBLICATIONS

Chen et al., A Homogeneous, Ligase-Mediated DNA Diagnostic Test, Genome Research, 1998, vol. 8, pp. 549-556.*

(Continued)

*Primary Examiner* — Young J Kim
(74) *Attorney, Agent, or Firm* — Kilpatrick Townsend & Stockton LLP

(57) ABSTRACT

The invention relates to methods and devices for analyzing single molecules, i.e. nucleic acids. Such single molecules may be derived from natural samples, such as cells, tissues, soil, air and water without separating or enriching individual components. In certain aspects of the invention, the methods and devices are useful in performing nucleic acid sequence analysis by probe hybridization.

26 Claims, 11 Drawing Sheets

U.S. PATENT DOCUMENTS

Figure 1:
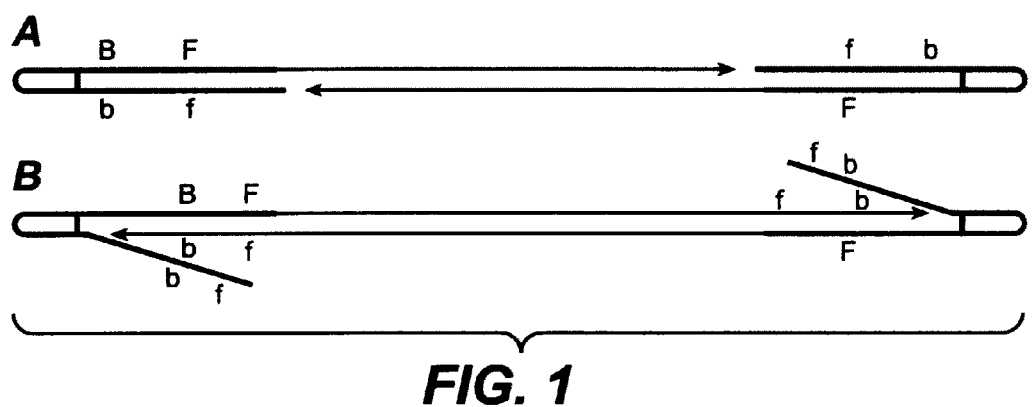

| | | | |
|---|---|---|---|
| 7,064,197 | B1 | 6/2006 | Rabbani |
| 7,276,720 | B2 | 10/2007 | Ulmer |
| 7,384,737 | B2 | 6/2008 | Barnes |
| 7,544,473 | B2 | 6/2009 | Brennar |
| 2002/0004204 | A1 | 1/2002 | O'Keefe |
| 2002/0042048 | A1 | 4/2002 | Drmanac |
| 2002/0055100 | A1 | 5/2002 | Kawashima |
| 2002/0197621 | A1 | 12/2002 | Drmanac |
| 2003/0215821 | A1* | 11/2003 | Gunderson et al. ............ 435/6 |
| 2004/0002090 | A1 | 1/2004 | Mayer |
| 2004/0229221 | A1 | 11/2004 | Schon |
| 2004/0248144 | A1 | 12/2004 | Mir |
| 2005/0019776 | A1 | 1/2005 | Callow |
| 2005/0037356 | A1 | 2/2005 | Gullberg |
| 2005/0042649 | A1 | 2/2005 | Balasubramanian |
| 2005/0100939 | A1 | 5/2005 | Namsaraev |
| 2005/0191656 | A1 | 9/2005 | Drmanac |
| 2005/0214840 | A1 | 9/2005 | Chen |
| 2005/0244863 | A1 | 11/2005 | Mir |
| 2006/0012793 | A1 | 1/2006 | Harris |
| 2006/0024681 | A1 | 2/2006 | Smith |
| 2007/0015182 | A1 | 1/2007 | Abarzua |
| 2007/0072208 | A1 | 3/2007 | Drmanac |
| 2008/0318796 | A1 | 12/2008 | Drmanac |
| 2009/0099041 | A1 | 4/2009 | Church |
| 2009/0137414 | A1 | 5/2009 | Drmanac |
| 2009/0264299 | A1 | 10/2009 | Drmanac |

FOREIGN PATENT DOCUMENTS

| | | |
|---|---|---|
| JP | 4-304900 | 10/1992 |
| WO | WO-89/10977 | 11/1989 |
| WO | WO-90/03382 | 4/1990 |
| WO | WO 95/09248 | 4/1995 |
| WO | WO-95/09248 | 4/1995 |
| WO | WO-96/17957 | 6/1996 |
| WO | WO-98/31836 | 7/1998 |
| WO | WO 99/09217 | 2/1999 |
| WO | WO-99/09217 | 2/1999 |
| WO | WO-00/40758 | 7/2000 |
| WO | WO 00/40758 | 7/2000 |
| WO | WO 01/62982 | 8/2001 |
| WO | WO 02/074988 | 9/2002 |
| WO | WO-02/074988 | 9/2002 |
| WO | WO 2004027056 A2 * | 4/2004 |
| WO | WO 2004/072294 | 8/2004 |
| WO | WO 2005/040425 | 5/2005 |
| WO | WO 2005/047523 | 5/2005 |
| WO | WO 2005/078130 | 8/2005 |
| WO | WO 2005/080605 | 9/2005 |
| WO | WO 2005/082098 | 9/2005 |
| WO | WO 2005/093094 | 10/2005 |
| WO | WO 2005/116262 | 12/2005 |
| WO | WO 2006/007207 | 1/2006 |
| WO | WO 2006/040549 | 4/2006 |
| WO | WO 2006/055521 | 5/2006 |
| WO | WO 2006/073504 | 7/2006 |
| WO | WO 2006/084132 | 8/2006 |
| WO | WO 2007/014397 | 2/2007 |
| WO | WO 2007/025124 | 3/2007 |
| WO | WO 2007/061425 | 5/2007 |
| WO | WO 2007/062160 | 5/2007 |

OTHER PUBLICATIONS

Adessi et al., Nucleic Acids Res., 28(20):e87 (2000).
Andreadis et al., Nucleic Acids Res., 28(2):e5 (2000).
Breslauer et al., Proc. Natl. Acad. Sci. USA, 83:3746-3750 (1986).
Broude et al., Proc. Natl. Acad. Sci. USA, 91:3072-3076 (1994).
Cheng et al., Nat. Biotechnol., 16:541-546 (1998).
Cutler et al., Genome Res., 11:1913-1925 (2001).
Doing et al., J. Clin. Microbiol., 37(5):1582-1583 (1999).
Drmanac et al., Nucleic Acids Res., 14(11):4691-4692 (1986).
Drmanac et al., Nucleic Acids Res., 19(21):5839-5842 (1991).
Fitzgerald et al., Nucleic Acids Res., 20(14):3753-3762 (1992).
Gunderson et al., Genome Res., 8:1142-1153 (1998).
Hacia et al., Genome Res., 8:1245-1258 (1998).
Housby et al., Nucleic Acids Res., 26(18):4259-4266 (1998).
Inouye et al., J. Clin. Microbiol., 28(6):1469-1472 (1990).
Marks, Clin. Chem., 48(11):2008-2016 (2002).
Maxam et al., Proc. Natl. Acad. Sci. USA, 74(2):560-564 (1977).
Meier-Ewert et al., Nucleic Acids Res., 26(9):2216-2223 (1998).
Nikiforov et al., Nucleic Acids Res., 22(20):4167-4175 (1994).
Pease et al., Proc. Natl. Acad. Sci., 91:5022-5026 (1994).
Radnedge et al., Appl. Environ. Microbiol., 67(8):3759-3762 (2001).
Radnedge et al., Microbiology, 148:1687-1698 (2002).
Reichert et al., J. Cell Sci., 96:219-230 (1990).
Ronaghi, Genome Res., 11:3-11 (2001).
Saiki et al., Proc. Natl. Acad. Sci. USA, 86:6230-6234 (1989).
Sanger et al., Proc. Natl. Acad. Sci. USA, 74(12):5463-5467 (1977).
Scholler et al., Nucleic Acids Res., 23(19):3842-3849 (1995).
Strezoska et al., Proc. Natl. Acad. Sci. USA, 88:10089-10093 (1991).
Sugimoto et al., Nucleic Acids Res., 24(22):4501-4505 (1996).
Wallace et al., Nucleic Acids Res., 6(11):3543-3557 (1979).
Wang et al., Science, 280:1077-1082 (1998).
Zhang et al., Nucleic Acids Res., 19(14):3929-3933 (1991).
Abath et al., Biotechniques, 33(6):1210, 1212, 1214 (2002).
Abney et al., Biophys. J., 61:542-552 (1992).
Ambrose et al., Cytometry, 36:224-231 (1999).
Axelrod, Traffic, 2:764-774 (2001).
Bains et al., J. Theor. Biol., 135:303-307 (1988).
Beaucage et al., Tetrahedron Lett., 22(20):1859-1862 (1981).
Chee et al., Science, 274:610-614 (1996).
Dahlen et al., Mol. Cell. Probes, 1:159-168 (1987).
Dianzani et al., Genomics, 11:48-53 (1991).
Didenko, Biotechniques, 31:1106-1121 (2001).
Doty et al., Proc. Natl. Acad. Sci. USA, 46:461-476 (1960).
Drmanac et al., DNA Cell Biol., 9(7):527-534 (1990).
Drmanac et al., Electrophoresis, 13:566-573 (1992).
Drmanac et al., Genomics, 4:114-128 (1989).
Drmanac et al., Genomics, 37:29-40 (1996).
Drmanac et al., Intl. J. Genome Res., 1(1):59-79 (1992).
Drmanac et al., J. Biolmol. Struct. Dyn., 8(5):1085-1102 (1991).
Drmanac et al., Methods Enzymol., 303:165-178 (1999).
Drmanac et al., Nat. Biotechnol., 16:54-58 (1998).
Drmanac et al., Science, 260:1649-1652 (1993).
Drmanac et al., Scientia Yugoslaviea, 16(1-2):97-107 (1990).
Fodor et al., Science, 251:767-773 (1991).
Goodchild, Bioconjug. Chem., 1(3):165-187 (1990).
Ha, Methods, 25:78-86 (2001).
Hacia et al., Nat. Genet., 14:441-447 (1996).
Hoheisel et al., Cell, 73:109-120 (1993).
Hoheisel et al., J. Mol. Biol., 220:903-914 (1991).
Holley et al., Science, 147:1462-1465 (1965).
Hunkapiller et al., Science, 254:59-67 (1991).
Iqbal et al., Biosens. Bioelectron., 15:549-578 (2000).
Keller et al., Anal. Biochem., 170:441-450 (1988).
Keller et al., Anal. Biochem., 177:392-395 (1989).
Khrapko et al., FEBS Lett., 256:118-122 (1989).
Klostermeier et al., Biopolymers, 61:159-179 (2002).
Kozal et al., Nat. Med., 2(7):753-759 (1996).
Lockhart et al., Nat. Biotechnol., 14:1675-1680 (1996).
Michiels et al., Comput. Appl. Biosci., 3(3):203-210 (1987).
Milosavljevic et al., Genome Res., 6:132-141 (1996).
Milosavljevic et al., Genomics, 37:77-86 (1996).
Nichols et al., Nature, 369:492-493 (1994).
Poustka et al., Trends Genet., 2:174-179 (1986).
Southern et al., Genomics, 13:1008-1017 (1992).
Tokunaga et al., Biochem. Biphys. Res. Commun., 235:47-53 (1997).
Wetmur, Crit. Rev. Biochem. Mol. Biol., 26:227-259 (1991).
Wilson et al., Mol. Cell. Probes, 16:119-127 (2002).
Chen et al., "A Homogeneous, Ligase-Mediated DNA Diagnostic Test", *Genome Research*, vol. 8, No. 5, May 1998, pp. 549-556.
Dramanac et al., "Sequencing by Hybridization (SBH): Advantages, Achievements, and Opportunities" *Advances in Biochemical Engineering*, vol. 77, 2002, pp. 75-101.
European Search Report, European Application No. 04715167, dated May 8, 2006.
Blanco et al., "Highly efficient DNA synthesis by the phage phi 29 DNA polymerase," J. Biol. Chem., v. 264, issue 15, p. 8935-8940 (1989).

Brenner et al, "Gene Expression Analysis by Massivly Parallel Signature Sequencing (MPSS) on Microbead Arrays," Nature Biotechnology, v. 18, p. 630-634 (2000).

Li, M. et al., "BEAMing up for detection and quantification of rare sequence variants," Nature Methods, vol. 3, pp. 95-97 (2006).

Metzker, "Emerging Technologies in DNA Sequencing," Genome Research, 15: 1767-1776 (2005.

Shendure et al, "Accurate multiplex polony sequencing of an evolved bacterial genome," Science, 309: 1728-1732 (2005).

Shendure et al, "Advanced Sequencing Technologies: Methods and Goals," Nature Reviews Genetics, vol. 5, pp. 335-344 (2004).

Tringe et al, "Metagenomics: DNA Sequencing of Environmental Samples," Nature Reviews Genetics, vol. 6, pp. 805-814 (2005.

Vingron et al., "Sequence Alignment and Penalty Choice Review of Concepts, Case Studies and Implications," J. Mol. Biol, vol. 235, issue 1, pp. 1-12 (1994).

* cited by examiner

Adaptor Sequences:
Ad-F    5' OH-GGGGTTACACAATATCATCTACTGCACTGA-3' OH  (SEQ. ID NO: 22)
Ad-f    3' dd-CCCCAATGTGTTATAGTAGATGACGTGACTNNNNNNNN-5' OH  (SEQ. ID NO: 23)
Ad-b    5' P-TCAGTAATAGCCTTAGACCGATTTCAGAAC-3' dd  (SEQ. ID NO: 24)
Ad-B    3' dd-NNNNNNNNAGTCATTATCGGAATCTGGCTAAAGTCTTG-5' P  (SEQ. ID NO: 25)

Arrangement of Adapters and Genomic DNA (Black Bar):

***Arrow is pointing from 5' to 3'

F and B Adapters Cannot Ligate to Each Other:

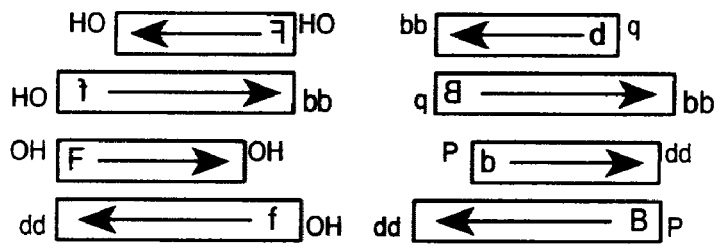

F Cannot Ligate to Itself:

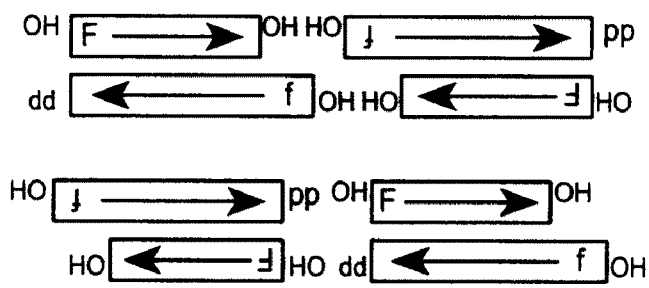

B Cannot Ligate to Itself:

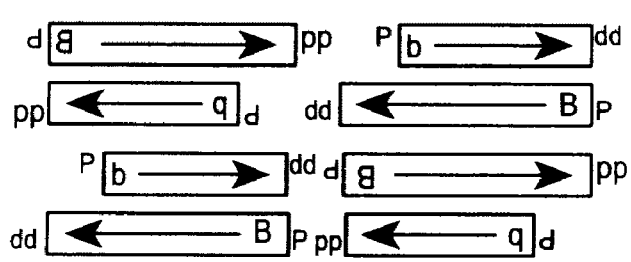

FIG. 2

Invader Mediated Isothermal DNA Amplification Schema

```
            TATATABBBBBBBBBBBBBBBBBBBBBBBBBBBBBBBBBB  displaced strand  SEQ. ID NO:26
DDDDDDDDDATATATBBB(SEQ ID NO: 27)    ....PPPPPPPPPPPPPPPPPP  primer 2  SEQ. ID NO:28
  Primer 1  PPPPPPPPPPPPPPPPPP............ SEQ. ID NO:29
            ATATATBBBBBBBBBBBBBBBBBBBBBBBBBBBBBBBBBBBB   SEQ. ID NO:30
```

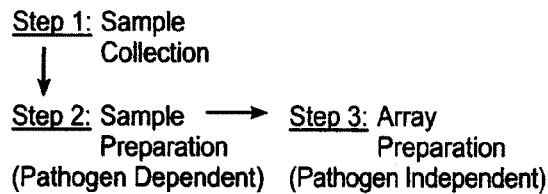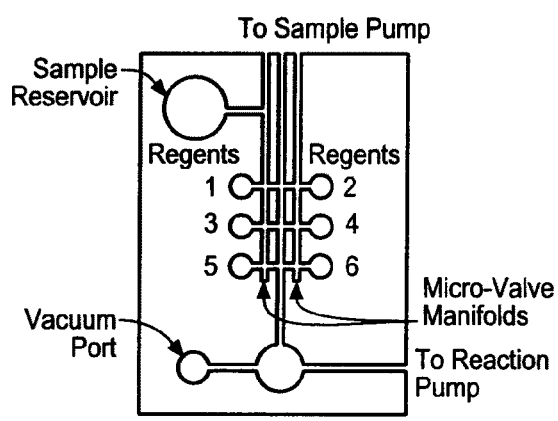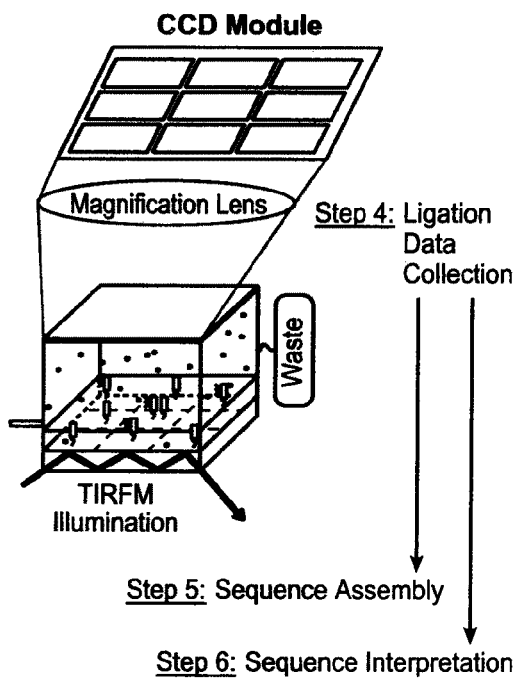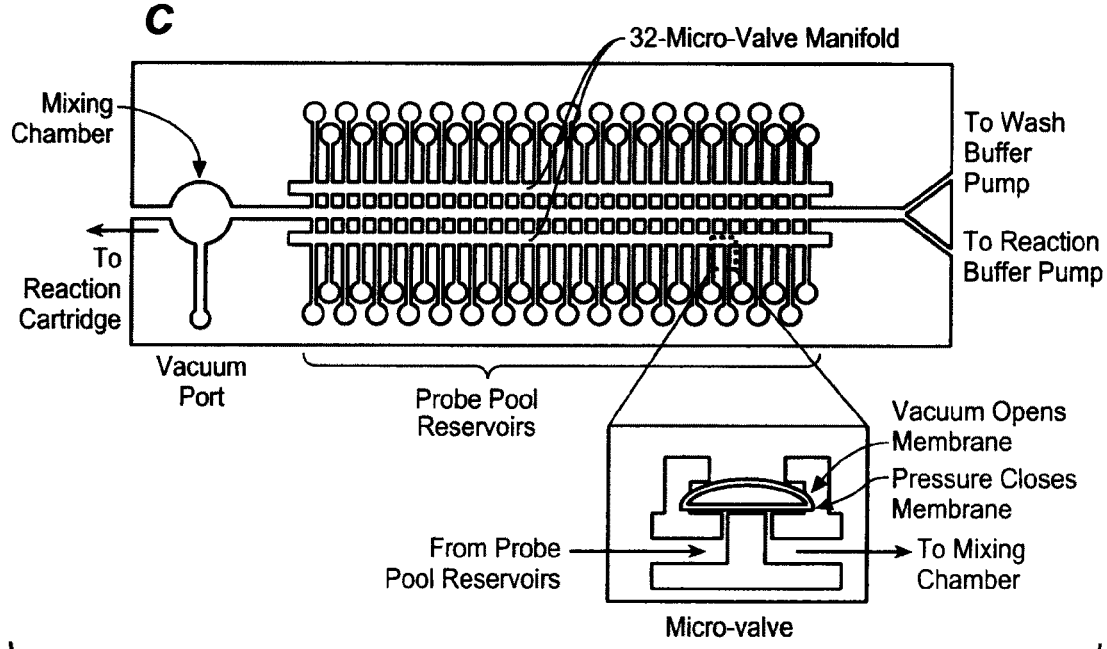
FIG. 11

SEQUENCE LISTING

<160> NUMBER OF SEQ ID NOS: 55

<210> SEQ ID NO 1
<211> LENGTH: 30
<212> TYPE: DNA
<213> ORGANISM: Artificial Sequence
<220> FEATURE:
<223> OTHER INFORMATION: Primer sequence

<400> SEQUENCE: 1
ccgatcttag caacgcatac aaacgtcagt                30

<210> SEQ ID NO 2
<211> LENGTH: 30
<212> TYPE: DNA
<213> ORGANISM: Artificial Sequence
<220> FEATURE:
<223> OTHER INFORMATION: Primer sequence

<400> SEQUENCE: 2
ttcgacacgt ccaggaacgt gcttcaatga                                    30

<210> SEQ ID NO 3
<211> LENGTH: 30
<212> TYPE: DNA
<213> ORGANISM: Artificial Sequence
<220> FEATURE:
<223> OTHER INFORMATION: Primer sequence

<400> SEQUENCE: 3
gtcaactgta cctattcagt cactactcat                                    30

<210> SEQ ID NO 4
<211> LENGTH: 26
<212> TYPE: DNA
<213> ORGANISM: Artificial Sequence
<220> FEATURE:
<223> OTHER INFORMATION: Primer sequence

<400> SEQUENCE: 4
cagcagtacg attcatactt gcatat                                        26

<210> SEQ ID NO 5
<211> LENGTH: 50
<212> TYPE: DNA
<213> ORGANISM: Artificial Sequence
<220> FEATURE:
<223> OTHER INFORMATION: Primer sequence

<400> SEQUENCE: 5
ttcgacacgt ccaggaacgt gcttcaatga actgacgttt gtatgcgttg              50

<210> SEQ ID NO 6
<211> LENGTH: 9
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(3)
<223> OTHER INFORMATION: n = g, a, t, or c, or a universal base

<400> SEQUENCE: 6 nnntgtatg                                                            9

<210> SEQ ID NO 7
<211> LENGTH: 9
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(3)
<223> OTHER INFORMATION: n = g, a, t, or c, or a universal base

<400> SEQUENCE: 7 nnntgtaag                                                            9

```
<210> SEQ ID NO 8
<211> LENGTH: 7
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (6)..(7)
<223> OTHER INFORMATION: n=g, a, t, or c, or a universal base

<400> SEQUENCE: 8 cgttgnn                                                                    7

<210> SEQ ID NO 9
<211> LENGTH: 7
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (6)..(7)
<223> OTHER INFORMATION: n = g, a, t, or c, or a universal base

<400> SEQUENCE: 9 cgatgnn                                                                    7

<210> SEQ ID NO 10
<211> LENGTH: 9
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(3)
<223> OTHER INFORMATION: n = g, a, t, or c, or a universal base

<400> SEQUENCE: 10 nnncacgtt                                                                  9

<210> SEQ ID NO 11
<211> LENGTH: 9
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(3)
<223> OTHER INFORMATION: n = g, a, t, or c, or a universal base

<400> SEQUENCE: 11 nnncacgat                                                                  9

<210> SEQ ID NO 12
<211> LENGTH: 7
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (6)..(7)
<223> OTHER INFORMATION: n = g, a, t, or c, or a universal base

<400> SEQUENCE: 12 cctggnn                                                                    7
```

```
<210> SEQ ID NO 13
<211> LENGTH: 7
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (6)..(7)
<223> OTHER INFORMATION: n = g, a, t, or c, or a universal base

<400> SEQUENCE: 13 ccaggnn                                                              7

<210> SEQ ID NO 14
<211> LENGTH: 9
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(3)
<223> OTHER INFORMATION: n = g, a, t, or c, or a universal base

<400> SEQUENCE: 14 nnngactga                                                            9

<210> SEQ ID NO 15
<211> LENGTH: 9
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(3)
<223> OTHER INFORMATION: n = g, a, t, or c, or a universal base

<400> SEQUENCE: 15 nnngactca                                                            9

<210> SEQ ID NO 16
<211> LENGTH: 7
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (6)..(7)
<223> OTHER INFORMATION: n = g, a, t, or c, or a universal base

<400> SEQUENCE: 16 ataggnn                                                              7

<210> SEQ ID NO 17
<211> LENGTH: 7
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (6)..(7)
<223> OTHER INFORMATION: n = g, a, t, or c, or a universal base

<400> SEQUENCE: 17 atcggnn                                                              7
```

<210> SEQ ID NO 18
<211> LENGTH: 9
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(3)
<223> OTHER INFORMATION: n = g, a, t, or c, or a universal base

<400> SEQUENCE: 18 nnngtatga                                                                 9

<210> SEQ ID NO 19
<211> LENGTH: 9
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(3)
<223> OTHER INFORMATION: n = g, a, t, or c, or a universal base

<400> SEQUENCE: 19 nnngtatca                                                                 9

<210> SEQ ID NO 20
<211> LENGTH: 7
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (6)..(7)
<223> OTHER INFORMATION: n = g, a, t, or c, or a universal base

<400> SEQUENCE: 20 atcgtnn                                                                   7

<210> SEQ ID NO 21
<211> LENGTH: 7
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (6)..(7)
<223> OTHER INFORMATION: n = g, a, t, or c, or a universal base

<400> SEQUENCE: 21 atggtnn                                                                   7

<210> SEQ ID NO 22
<211> LENGTH: 30
<212> TYPE: DNA
<213> ORGANISM: Artificial Sequence
<220> FEATURE:
<223> OTHER INFORMATION: primer sequence

<400> SEQUENCE: 22
ggggttacac aatatcatct actgcactga                                         30

<210> SEQ ID NO 23
<211> LENGTH: 37

```
<212> TYPE: DNA
<213> ORGANISM: Artificial Sequence
<220> FEATURE:
<223> OTHER INFORMATION: primer sequence
<220> FEATURE:
<221> NAME/KEY: misc_feature
<222> LOCATION: (31)..(37)
<223> OTHER INFORMATION: n = g, a, t, or c, or a universal base

<400> SEQUENCE: 23
ccccaatgtg ttatagtaga tgacgtgact nnnnnnn                             37

<210> SEQ ID NO 24
<211> LENGTH: 30
<212> TYPE: DNA
<213> ORGANISM: Artificial Sequence
<220> FEATURE:
<223> OTHER INFORMATION: primer sequence

<400> SEQUENCE: 24
tcagtaatag ccttagaccg atttcagaac                                      30

<210> SEQ ID NO 25
<211> LENGTH: 37
<212> TYPE: DNA
<213> ORGANISM: Artificial Sequence
<220> FEATURE:
<223> OTHER INFORMATION: primer sequence
<220> FEATURE:
<221> NAME/KEY: misc_feature
<222> LOCATION: (1)..(7)
<223> OTHER INFORMATION: n = g, a, t, or c, or a universal base

<400> SEQUENCE: 25
nnnnnnnagt cattatcgga atctggctaa agtcttg                              37

<210> SEQ ID NO 26
<211> LENGTH: 46
<212> TYPE: DNA
<213> ORGANISM: Artificial Sequence
<220> FEATURE:
<223> OTHER INFORMATION: displaced strand
<220> FEATURE:
<221> NAME/KEY: misc_feature
<222> LOCATION: (7)..(42)
<223> OTHER INFORMATION: n = g, a, t, or c, or a universal base
<220> FEATURE:
<221> NAME/KEY: misc_feature
<222> LOCATION: (43)..(46)
<223> OTHER INFORMATION: n is a, c, g, or t

<400> SEQUENCE: 26
tatatannnn nnnnnnnnn nnnnnnnnnn nnnnnnnnnn nnnnnn                     46

<210> SEQ ID NO 27
<211> LENGTH: 18
<212> TYPE: DNA
<213> ORGANISM: Artificial Sequence
<220> FEATURE:
<223> OTHER INFORMATION: primer 2
<220> FEATURE:
<221> NAME/KEY: misc_feature
<222> LOCATION: (1)..(9)
<223> OTHER INFORMATION: n = g, a, t, or c, or a universal base
<220> FEATURE:
<221> NAME/KEY: misc_feature
<222> LOCATION: (16)..(18)
<223> OTHER INFORMATION: n = g, a, t, or c, or a universal base

<400> SEQUENCE: 27
nnnnnnnnna tatatnnn                                                   18
```

<210> SEQ ID NO 28
<211> LENGTH: 17
<212> TYPE: DNA
<213> ORGANISM: Artificial Sequence
<220> FEATURE:
<223> OTHER INFORMATION: primer 2
<220> FEATURE:
<221> NAME/KEY: misc_feature
<222> LOCATION: (1)..(17)
<223> OTHER INFORMATION: n = g, a, t, or c, or a universal base

<400> SEQUENCE: 28
nnnnnnnnnn nnnnnnn                                                    17

<210> SEQ ID NO 29
<211> LENGTH: 17
<212> TYPE: DNA
<213> ORGANISM: Artificial Sequence
<220> FEATURE:
<223> OTHER INFORMATION: Primer 1
<220> FEATURE:
<221> NAME/KEY: misc_feature
<222> LOCATION: (1)..(17)
<223> OTHER INFORMATION: n = g, a, t, or c, or a universal base

<400> SEQUENCE: 29
nnnnnnnnnn nnnnnnn                                                    17

<210> SEQ ID NO 30
<211> LENGTH: 48
<212> TYPE: DNA
<213> ORGANISM: Artificial Sequence
<220> FEATURE:
<223> OTHER INFORMATION: Amplification Schema
<220> FEATURE:
<221> NAME/KEY: misc_feature
<222> LOCATION: (7)..(42)
<223> OTHER INFORMATION: n = g, a, t, or c, or a universal base
<220> FEATURE:
<221> NAME/KEY: misc_feature
<222> LOCATION: (43)..(48)
<223> OTHER INFORMATION: n is a, c, g, or t

<400> SEQUENCE: 30
atatatnnnn nnnnnnnnnn nnnnnnnnnn nnnnnnnnnn nnnnnnnn                  48

<210> SEQ ID NO 31
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 31
gaccgtaaat                                                            10

<210> SEQ ID NO 32
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 32
accgtaaatc                                                            10

<210> SEQ ID NO 33
<211> LENGTH: 10

```
<212> TYPE: DNA
<213> ORGANISM: Artificial Sequence
<220> FEATURE:
<223> OTHER INFORMATION: Positive 10-mer Probe

<400> SEQUENCE: 33
ccgtaaatcg                                                                10

<210> SEQ ID NO 34
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 34
cgtaaatcgg                                                                10

<210> SEQ ID NO 35
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 35
gtaaatcggt                                                                10

<210> SEQ ID NO 36
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 36
taaatcggta                                                                10

<210> SEQ ID NO 37
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 37
aaatcggtat                                                                10

<210> SEQ ID NO 38
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 38
aatcggtatc                                                                10

<210> SEQ ID NO 39
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 39
atcggtatca                                                                10
```

```
<210> SEQ ID NO 40
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 40
tcggtatcaa                                                              10

<210> SEQ ID NO 41
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 41
cggtatcaag                                                              10

<210> SEQ ID NO 42
<211> LENGTH: 10
<212> TYPE: DNA
<213> ORGANISM: Artificial Sequence
<220> FEATURE:
<223> OTHER INFORMATION: Positive 10-mer Probe

<400> SEQUENCE: 42
ggtatcaagc                                                              10

<210> SEQ ID NO 43
<211> LENGTH: 10
<212> TYPE: DNA
<213> ORGANISM: Artificial Sequence
<220> FEATURE:
<223> OTHER INFORMATION: Overlapping Positive 10-mer Probe

<400> SEQUENCE: 43
gaccgtaaat                                                              10

<210> SEQ ID NO 44
<211> LENGTH: 10
<212> TYPE: DNA
<213> ORGANISM: Artificial Sequence
<220> FEATURE:
<223> OTHER INFORMATION: Overlapping Positive 10-mer Probe

<400> SEQUENCE: 44
accgtaaatc                                                              10

<210> SEQ ID NO 45
<211> LENGTH: 10
<212> TYPE: DNA
<213> ORGANISM: Artificial Sequence
<220> FEATURE:
<223> OTHER INFORMATION: Overlapping Positive 10-mer Probe

<400> SEQUENCE: 45
ccgtaaatcg                                                              10

<210> SEQ ID NO 46
<211> LENGTH: 10
<212> TYPE: DNA
<213> ORGANISM: Artificial Sequence
<220> FEATURE:
<223> OTHER INFORMATION: Overlapping Positive 10-mer Probe
```

```
<400> SEQUENCE: 46
cgtaaatcgg                                                              10

<210> SEQ ID NO 47
<211> LENGTH: 10
<212> TYPE: DNA
<213> ORGANISM: Artificial Sequence
<220> FEATURE:
<223> OTHER INFORMATION: Overlapping Positive 10-mer Probe

<400> SEQUENCE: 47
gtaaatcggt                                                              10

<210> SEQ ID NO 48
<211> LENGTH: 10
<212> TYPE: DNA
<213> ORGANISM: Artificial Sequence
<220> FEATURE:
<223> OTHER INFORMATION: Overlapping Positive 10-mer Probe

<400> SEQUENCE: 48
taaatcggta                                                              10

<210> SEQ ID NO 49
<211> LENGTH: 10
<212> TYPE: DNA
<213> ORGANISM: Artificial Sequence
<220> FEATURE:
<223> OTHER INFORMATION: Overlapping Positive 10-mer Probe

<400> SEQUENCE: 49
aaatcggtat                                                              10

<210> SEQ ID NO 50
<211> LENGTH: 10
<212> TYPE: DNA
<213> ORGANISM: Artificial Sequence
<220> FEATURE:
<223> OTHER INFORMATION: Overlapping Positive 10-mer Probe

<400> SEQUENCE: 50
aatcggtatc                                                              10

<210> SEQ ID NO 51
<211> LENGTH: 10
<212> TYPE: DNA
<213> ORGANISM: Artificial Sequence
<220> FEATURE:
<223> OTHER INFORMATION: Overlapping Positive 10-mer Probe

<400> SEQUENCE: 51
atcggtatca                                                              10

<210> SEQ ID NO 52
<211> LENGTH: 10
<212> TYPE: DNA
<213> ORGANISM: Artificial Sequence
<220> FEATURE:
<223> OTHER INFORMATION: Overlapping Positive 10-mer Probe

<400> SEQUENCE: 52
tcggtatcaa                                                              10

<210> SEQ ID NO 53
<211> LENGTH: 10
```

```
<212> TYPE: DNA
<213> ORGANISM: Artificial Sequence
<220> FEATURE:
<223> OTHER INFORMATION: Overlapping Positive 10-mer Probe

<400> SEQUENCE: 53
cggtatcaag                                                                     10

<210> SEQ ID NO 54
<211> LENGTH: 10
<212> TYPE: DNA
<213> ORGANISM: Artificial Sequence
<220> FEATURE:
<223> OTHER INFORMATION: Overlapping Positive 10-mer Probe

<400> SEQUENCE: 54
ggtatcaagc                                                                     10

<210> SEQ ID NO 55
<211> LENGTH: 21
<212> TYPE: DNA
<213> ORGANISM: Artificial Sequence
<220> FEATURE:
<223> OTHER INFORMATION: Assembled Sequence

<400> SEQUENCE: 55
gaccgtaaat cggtatcaag c                                                        21
```

RANDOM ARRAY DNA ANALYSIS BY HYBRIDIZATION

1. CROSS-REFERENCE TO RELATED APPLICATIONS

This application is a U.S. National Phase Application pursuant to 35 U.S.C. 371 of International Application No. PCT/US04/006022, which was filed Feb. 26, 2004, claiming benefit of priority of U. S. Provisional Patent Application No. 60/450,566, which was filed Feb. 26, 2003. The entire disclosure of each of the foregoing applications is incorporated herein by reference. Related subject matter is disclosed in co-owned, co-pending U. S. patent application Ser. No. 10/738,108, which was filed Dec. 16, 2003, which claims the benefit of priority of U. S. Provisional Application No. 60/435,539, which was filed Dec. 20, 2002. These and all other patents and patent applications cited herein are herein incorporated by reference in their entirety.

2. BACKGROUND

2.1 Technical Field

The invention relates to methods for analyzing molecules and devices for performing such analysis. The methods and devices allow reliable analysis of a single molecule of nucleic acids. Such single molecules may be derived from natural samples such as cells, tissues, soil, air, water, without separating or enriching individual components. In certain aspects of the invention, the methods and devices are useful in performing nucleic acid sequence analysis or nucleic acid quantification including gene expression.

2.3. Background

There are three established DNA sequencing technologies. The dominant sequencing method used today is based on Sanger's dideoxy chain termination process (Sanger et al., *Proc. Natl. Acad. Sci. USA* 74:5463 (1977) herein incorporated by reference in its entirety) and relies on various gel-based separation instruments ranging from manual systems to fully automated capillary sequencers. The Sanger process is technically difficult and is limited to read lengths of about 1 kb or less, requiring multiple reads to achieve high accuracy. A second method, pyrosequencing, also uses polymerase to generate sequence information by monitoring production of pyrophosphate generated during consecutive cycles in which specific DNA bases are tested for incorporation into the growing chain (Ronaghi, *Genome Res.* 11:3 (2001), herein incorporated by reference in its entirety). The method provides an elegant multi-well plate assay, but only for local sequencing of very short 10-50 base fragments. This read length restriction represents a serious limitation for sequence-based diagnostics.

Both of the above technologies represent direct sequencing methods in which each base position in a chain is determined sequentially by direct experimentation. Sequencing by hybridization (SBH) (U.S. Pat. No. 5,202,231; Drmanac et al., *Genomics* 4:114 (1989), both of which are herein incorporated by reference in their entirety), uses the fundamental life chemistry of base-specific hybridization of complementary nucleic acids to indirectly assemble the order of bases in a target DNA. In SBH, overlapping probes of known sequence are hybridized to sample DNA molecules and the resulting hybridization pattern is used to generate the target sequence using computer algorithms (co-owned, co-pending U.S. patent application Ser. No. 09/874,772; Drmanac et al, *Science* 260:1649-1652 (1993); Drmanac et al., *Nat. Biotech.* 16:54-58 (1998); Drmanac et al., "Sequencing and Fingerprinting DNA by Hybridization with Oligonucleotide Probes," In: *Encyclopedia of Analytical Chemistry*, pp. 5232-5237 (2000); Drmanac et al., "Sequencing by Hybridization (SBH): Advantages, Achievements, and Opportunities," In: *Advances in Biochemical Engineering/Biotechnology: Chip Technology*, Hoheisel, J. (Ed.), Vol. 76, pp. 75-98 (2002), all of which are herein incorporated by reference in their entirety). Probes or DNA targets may be arrayed in the form of high-density arrays (see, for example, Cutler et al., *Genome Res.* 11:1913-1925 (2001), herein incorporated by reference in its entirety). Advantages of the SBH method include experimental simplicity, longer read length, higher accuracy, and multiplex sample analysis in a single assay.

Currently, there is a critical need for new biodefense technologies that can quickly and accurately detect, analyze, and identify all potential pathogens in complex samples. Current pathogen detection technologies generally lack the sensitivity and selectivity to accurately identify trace quantities of pathogens in such samples and are often expensive and difficult to operate. In addition, in their current implementations, all three sequencing technologies require large quantities of sample DNA. Samples are usually prepared by one of several amplification methods, primarily PCR. These methods, especially SBH, can provide good sequence-based diagnostics of individual genes or mixtures of 2-5 genes, although with substantial cost associated with DNA amplification and array preparation. Thus, all current sequencing methods lack the speed and efficiency needed to provide at acceptable cost comprehensive sequence-based pathogen diagnostics and screening in complex biological samples. This creates a wide gap between current technical capacity and new sequencing needs. Ideally, a suitable diagnostics process should permit a simultaneous survey of all critical pathogens potentially present in environmental or clinical samples, including mixtures in which engineered pathogens are hidden among organisms.

The requirements for such comprehensive pathogen diagnostics include the need to sequence 10-100 critical genes or entire genomes simultaneously for hundreds of pathogens and to process thousands of samples. Ultimately, this will require sequencing 10-100 Mb of DNA per sample, or 100 Mb to 10 Gb of DNA per day for a lab performing continuous systematic surveys. Current sequencing methods have over 100 fold lower sequencing throughput and 100 fold higher cost than is required for such comprehensive pathogen diagnostics and pre-symptomatic surveys.

Current biosensor technologies use a variety of molecular recognition strategies, including antibodies, nucleic acid probes, aptamers, enzymes, bioreceptors, and other small molecule ligands (Iqbal et al., *Biosensors and Bioelectronics* 15:549-578 (2000), herein incorporated by reference in its entirety). Molecular recognition elements must be coupled to a reporter molecule or tag to allow positive detection events.

Both DNA hybridization and antibody-based technologies are already widely used in pathogen diagnostics. Nucleic acid-based technologies are generally more specific and sensitive than antibody-based detection, but can be time consuming and less robust (Iqbal et al., 2000, supra). DNA amplification (through PCR or cloning) or signal amplification is generally necessary to achieve reliable signal strength and accurate prior sequence knowledge is required to construct pathogen-specific probes. Although development of monoclonal antibodies has increased the specificity and reliability of immunoassays, the technology is relatively expensive and prone to false positive signals (Doing et al., *J. Clin. Microbiol.* 37:1582-1583 (1999); Marks, *Clin. Chem.* 48:2008-2016 (2002), both of which are herein incorporated by reference in their entirety). Other molecular recognition technologies such as phage display, aptamers and small molecule ligands are still in their early stages of development and not yet versatile enough to address all pathogen detection problems.

The main liability of all current diagnostic technologies is that they lack the sensitivity and versatility to detect and identify all potential pathogens in a sample. Weapons designers can easily engineer new biowarfare agents to foil most pathogen-specific probes or immunoassays. There is a clear urgent need for efficient sequence-based diagnostics.

To this end, Applicants have developed a high-efficiency genome sequencing system, random DNA array-based sequencing by hybridization (rSBH). rSBH can be useful for genomic sequence analysis of all genomes present in complex microbial communities as well as individual human genome sequencing. rSBH eliminates the need for DNA cloning or DNA separation and reduces the cost of sequencing using methods known in the art.

4. SUMMARY OF THE INVENTION

The present invention provides novel methods, compositions or mixtures and apparatuses capable of analyzing single molecules of DNA to rapidly and accurately sequence any long DNA fragment, mixture of fragments, entire gene, mixture of genes, mixtures of mRNAs, long segments of chromosomes, entire chromosomes, mixtures of chromosomes, entire genome, or mixtures of genomes. Additionally, the present invention provides methods for identifying a nucleic acid sequence within a target nucleic acid. Through consecutive transient hybridizations, accurate and extensive sequence information is obtained from the compiled data. In an exemplary embodiment, a single target molecule is transiently hybridized to a probe or population of probes. After the hybridization ceases to exist with one or more probes, the target molecule again is transiently hybridized to a next probe or population of probes. The probe or population of probes may be identical to those of the previous transient hybridization or they may be different. Compiling a series of consecutive bindings of the same single target molecule with one or more molecules of probe of the same type provides reliable measurements. Thus, because it is consecutively contacted with probes, a single target molecule can provide a sufficient amount of data to identify a sequence within the target molecule. By compiling the data, the nucleic acid sequence of the entire target molecule can be determined.

Further provided by the present invention are methods, compositions and apparatuses for analyzing and detecting pathogens present in complex biological samples at the single organism level and identifying all virulence controlling genes.

The present invention provides a method of analyzing a target molecule comprising the steps of:
a) contacting the target molecule with one or more probe molecules in a series of consecutive binding reactions, wherein each association produces an effect on the target molecule or the probe molecule(s); and
b) compiling the effects of the series of consecutive binding reactions.

The present invention further provides a method of analyzing a target molecule comprising the steps of:
a) contacting the target molecule with one or more probe molecules in a series of consecutive hybridization/dissociation reactions, wherein each association produces an effect on the target molecule or the probe molecule(s); and
b) compiling the effects of the series of consecutive hybridization/dissociation reactions.

In certain embodiments, the series contains at least 5, at least 10, at least 25, at least 50, at least 100, or at least 1000 consecutive hybridization/dissociation or binding reactions. In one embodiment, the series contains at least 5 and less then 50 consecutive hybridization/dissociation or binding reactions.

The present invention includes embodiments wherein the probe molecule sequence or structure is known or is determinable. One such advantage of such embodiments is that they are useful in identifying a sequence in the target from the compiled effects of the one or more probes of known/determinable sequence. Furthermore, when multiple sequences that overlap have been identified within a target molecule, such identified, overlapping sequences can be used to sequence the target molecule.

The present invention further provides a method of analyzing a target molecule wherein the compilation of effects includes in the analysis a measurement involving time (i.e. length of time signal detected or the detection of signal over a preset time period, etc.). In certain embodiments, the effects are compiled by measuring the time that the target molecule(s) or probe molecule(s) produce a fluorescent signal.

Also provided by the present invention are methods wherein the effects are compiled by detecting a signal produced only upon hybridization or binding of the target molecule to a probe. Such methods include those wherein the effects are compiled by determining an amount of a time period that the signal is produced and those wherein the effects are compiled by determining the amount of signal produced. In certain embodiments, the target molecule(s) comprises a fluorescence resonance energy transfer (FRET) donor and the probe molecule(s) comprises a FRET acceptor. In other embodiments, the target molecule(s) comprises a FRET acceptor and the probe molecule(s) comprises a FRET donor.

The invention also provides methods wherein the effect on one or more probes is modification of the probe(s). In certain embodiments, the probes are ligated and the method further comprises detecting the ligated probes. The probes may be labeled with a nanotag.

In embodiments wherein the effect of hybridization or binding on the probe(s) is modification, wherein modifications caused by full-match hybridizations occur more frequently than modifications caused by mismatch hybridizations and a full-match is determinable by the detection of the occurrence of a relatively higher number of modifications.

The methods of the present invention include those wherein:
a) the target molecule is produced by fragmentation of a nucleic acid molecule;
b) the fragmentation is achieved through restriction enzyme digestion, ultrasound treatment, sodium hydroxide treatment, or low pressure shearing;
c) the target molecule is detectably labeled;
d) the target molecule and/or the probe molecule is detectably labeled with a label selected from the group consisting of a fluorescent label, a nanotag, a chemiluminescent label, a quantum dot, a quantum bead, a fluorescent protein, dendrimers with a fluorescent label, a micro-transponder, an electron donor molecule or molecular structure, and a light reflecting particle;
e) the label is detected with a charge-coupled device (CCD);

f) probe molecules having the same information region are each associated with the same detectable label;

g) one or more probe molecules comprise multiple labels;

h) the probe molecules are divided into pools, wherein each pool comprises at least two probe molecules having different information regions, and all probe molecules within each pool are associated with the same label which is unique to the pool as compared with every other pool;

i) a sequence of the target molecule is assembled by ordering overlapping probe sequences that hybridize to the target molecule;

j) a sequence of the target molecule is assembled by ordering overlapping probe sequences and determining the score/likelihood/probability of the assembled sequence from the hybridization efficiency of the incorporated probes;

k) the probes are each independently between 4 and 20 nucleotides in length in the informative region;

l) the probes are each independently between 4 and 100 nucleotides in length in the informative region;

m) the target sequence of an attached molecule has a length that is between about 20 and 20,000 bases;

n) one or more of the probes is comprised of at least one modified or universal base;

o) one or more of the probes is comprised of at least one universal base at a terminal position;

p) the hybridization conditions are effective to permit hybridization between the target molecule and only those probes that are perfectly complementary to a portion of the target molecule;

q) the contacting comprises at least about 10, at least about 100, at least about 1000, or at least about 10,000 probe molecules having informative regions that are distinct from each other; and/or r) fewer than 1000, 800, 600, 400, 200, 100, 75, 50, 25, or 10 target molecules are used.

In one embodiment, the method of the invention can be used for analyzing the microbial genomes in microbial biofilms and percent composition thereof. The biofilm community comprises microbes including *Leptospirillum ferriphilum* phylotype, *Ferrospirillum* sp., *Sulfobacillus thermosulfidooxidans* phylotype, archaea (including *Ferroplasma acidarmanus, Aplasma, Geneplasma* phylotype), and eukaryotes (including protests and fungi).

The invention further provides a method for isothermal amplification using strand displacement enzymes based on the formation of single stranded DNA for primer annealing by an invader oligonucleotide.

The invention further provides software that supports rSBH whole-genome (complex DNA samples) and can process as much as 3 Gbp to 10 Gbp of sequence.

The invention further provides for reagents and kits to simultaneously analyze a plurality of genes or diagnostic regions, process, and prepare pathogen DNA from blood samples.

The invention further provides for compositions comprising mixtures of probes, target nucleic acids, and ligating molecules to analyze a plurality of pathogen genes or diagnostic regions from blood, tissue, or environmental samples.

Numerous additional aspects and advantages of the invention will become apparent to those skilled in the art upon consideration of the following detailed description of the invention which describes presently preferred embodiments thereof.

5. DESCRIPTION OF THE DRAWINGS

The detailed description of the invention may be better understood in conjunction with the accompanying figures as follows:

FIG. 1 depicts adapter ligation and extension. Double stranded hairpin adapters (solid lines) are maintained in the hairpin form by cross-linked bases at the hairpin end. B and F represent bound primer and fixed primer sequences, respectively and their complementary sequences are in lower case. Genomic sequence is shown as thin lines. A) Non-phosphorylated adapters are ligated to genomic DNA resulting in nicks in the strand with free 3' ends (arrowhead). B) Extension from the 3' end produces a displaced strand and the replication of adapter sequences.

FIG. 2 depicts adapter design and attachment to a DNA fragment, wherein genomic DNA is represented by a solid black bar, F represents the free primer, B represents the bound primer, and f and b represent their complements, respectively.

Figure 3:
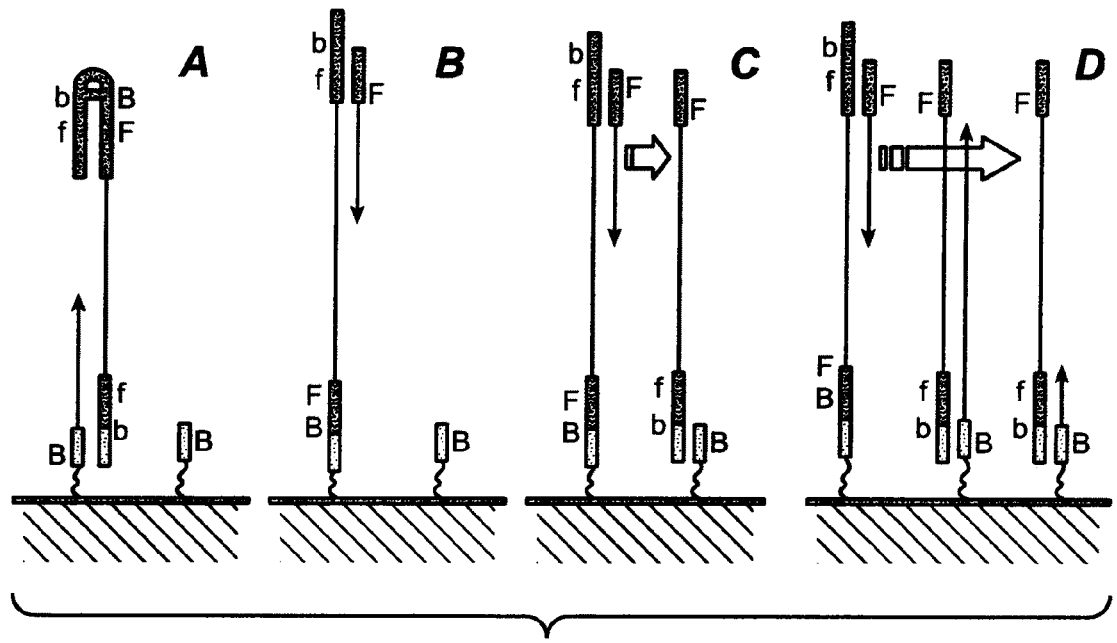

FIG. 3 depicts ampliot production on the chip surface. A) After melting of the adapter-captured genomic DNA, one strand is captured onto the surface of the slide by hybridization to bound primer B. Polymerase extension from primer B produces a double stranded molecule. B) The template strand is removed by heating and washing of the slide and a free primer F is introduced and extended along the fixed strand. C) Continuous strand displacement amplification by F results in the production of a strand that can move to nearby primer B hybridization sites. D) Displaced strands serve as template for extension from new primer B sites.

Figure 4:
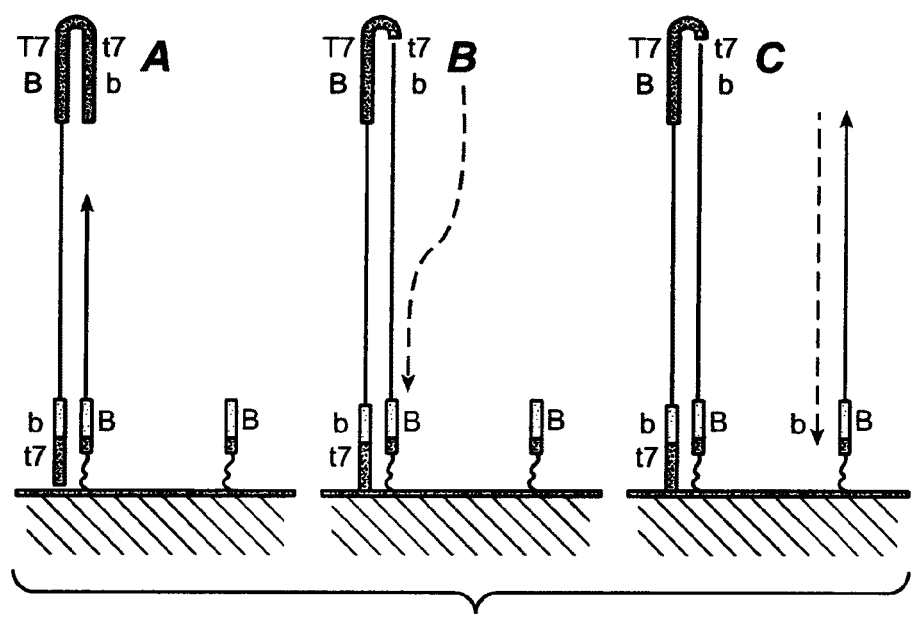

FIG. 4 depicts ampliot production using an RNA intermediate. T7 represents the T7 phage RNA polymerase promoter. A) The single stranded adapter region is hybridized to the bound primer B and extended to form a second strand by DNA polymerase resulting in the formation of a double stranded T7 promoter. B) T7 RNA polymerase produces an RNA copy (dashed line). C) The RNA then binds to a nearby primer B and cDNA is produced by reverse transcriptase. Duplex RNA is then destroyed by RNase H.

Figures 5, 6:
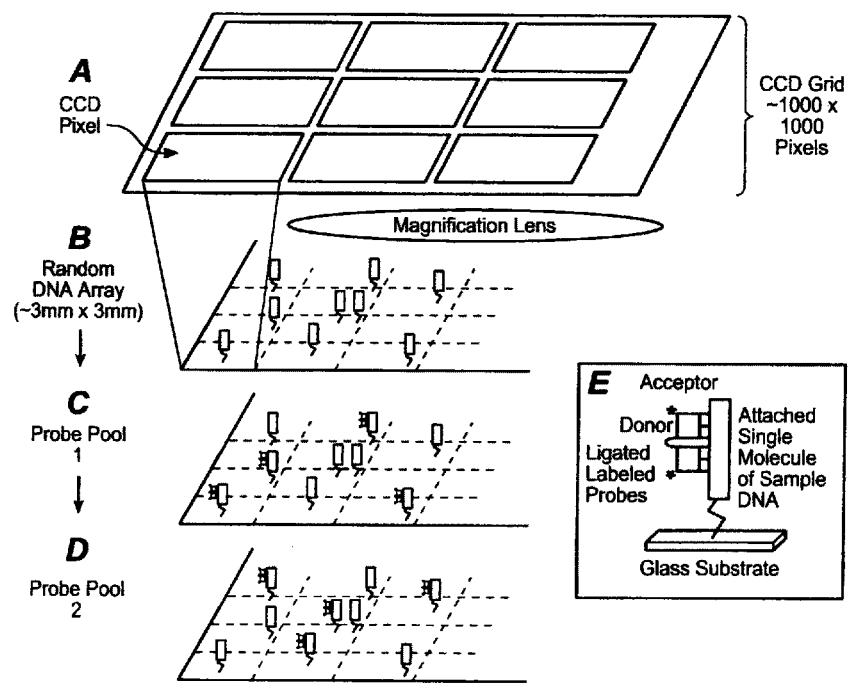

FIG. 5 depicts a schematic of the invader-mediated isothermal DNA amplification process.

FIG. 6 depicts the random array sequencing by hybridization (rSBH) process. From the top down: (a) A CCD camera is positioned above the reaction platform and a lens is used to magnify and focus on 1 µm² areas from the platform onto individual pixels of the CCD camera. (b) The array (~3 mm×3 mm) consists of 1 million or more 1 µm² areas, which act as virtual reaction wells (each corresponding to individual pixels of the CCD camera). Each pixel corresponds to the same location on the substrate. In a series of reactions in time, one CCD pixel can combine the data for several reactions, thereby creating the virtual reaction well. DNA samples are randomly digested and arrayed onto the surface of the reaction platform at an average concentration of one fragment per pixel. (c) The array is subjected to rSBH combinatorial ligation using one of several informational probe pools. The signals from each pixel are recorded. (d) Probes from the first pool are removed and the array is subjected to a second round of rSBH combinatorial ligation using a different pool or probes. (e) Insert showing molecular details of fluorescence resonance energy transfer (FRET) signal generation due to ligation of two adjacent and complementary probes whose compliment is represented by the target.

Figure 7:
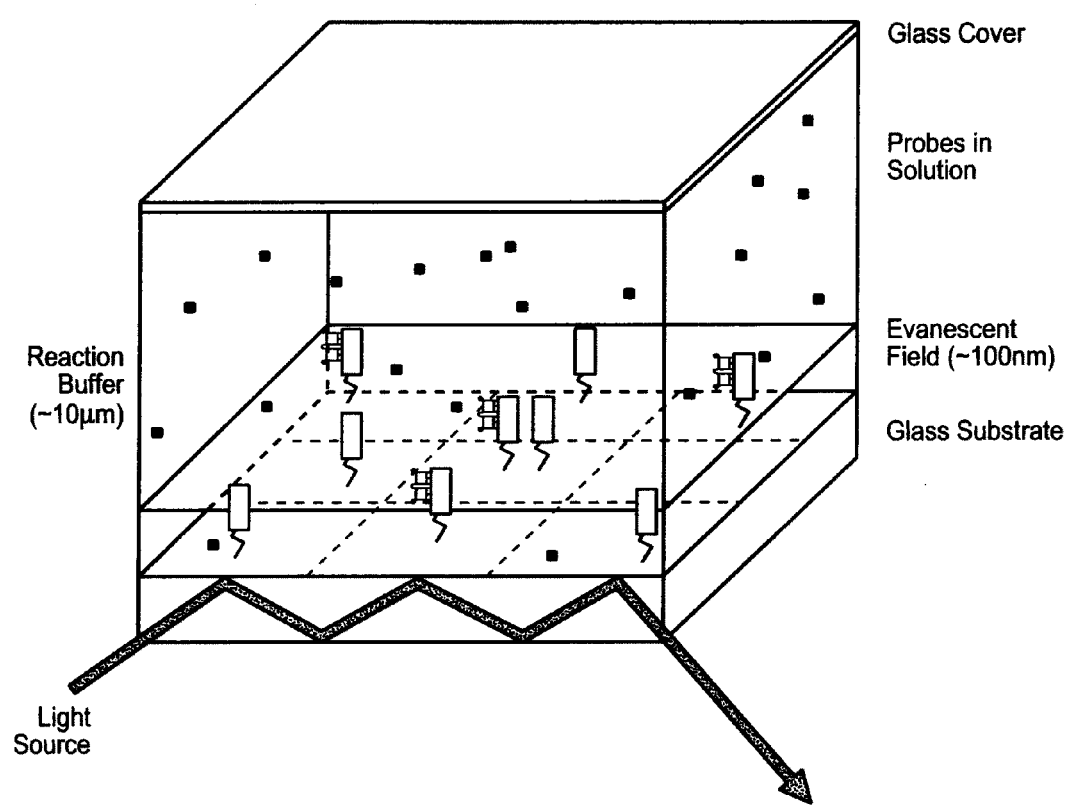

FIG. 7 depicts the rSBH reaction. The total internal reflection microscopy (TIRM) detection system creates an evanescent field in which enhanced excitation occurs only in the region immediately above the glass substrate. FRET signals are generated when probes are hybridized to the arrayed target and subsequently ligated, thus positioning the FRET pair within the evanescent field. Unligated probes do not give rise to detectable signals, whether they are free in solution or transiently hybridized to the target. Hence, the evanescent field of the TIRM system provided both intense signals within a desired plane while reducing background noise from unreacted probes.

Figure 8:
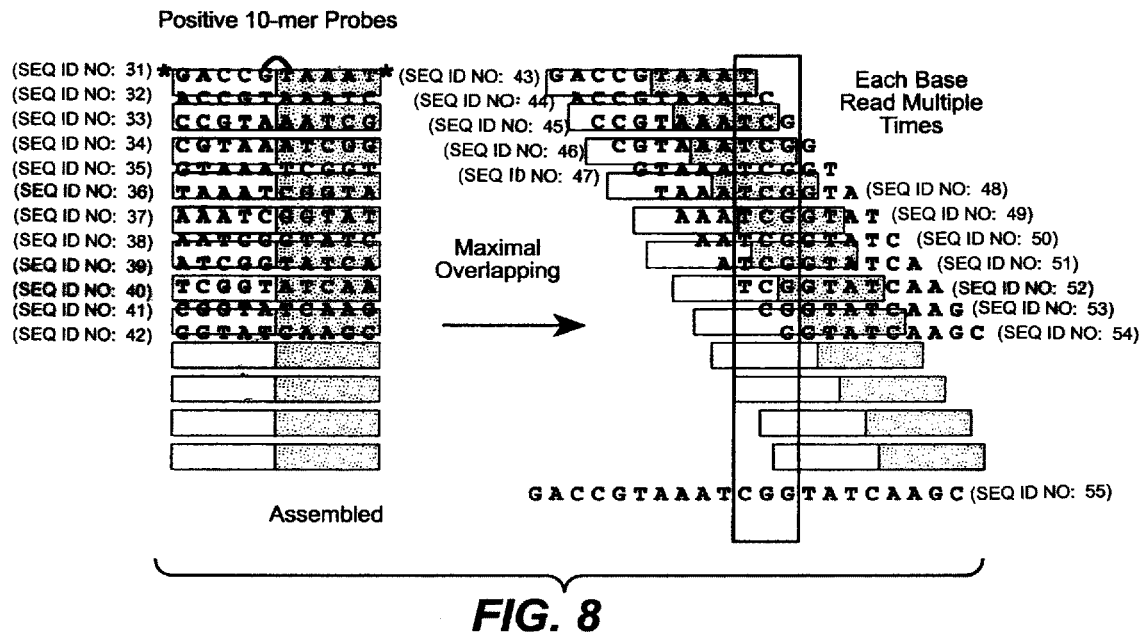

FIG. 8 depicts sequence assembly. In general, in the SBH process, the target sequence is assembled using overlapping positive probes. In this process each base is read several times (i.e. 10 times with 10-mer probes, etc.) which assures very high accuracy even if some probes are not correctly scored.

Figure 9:
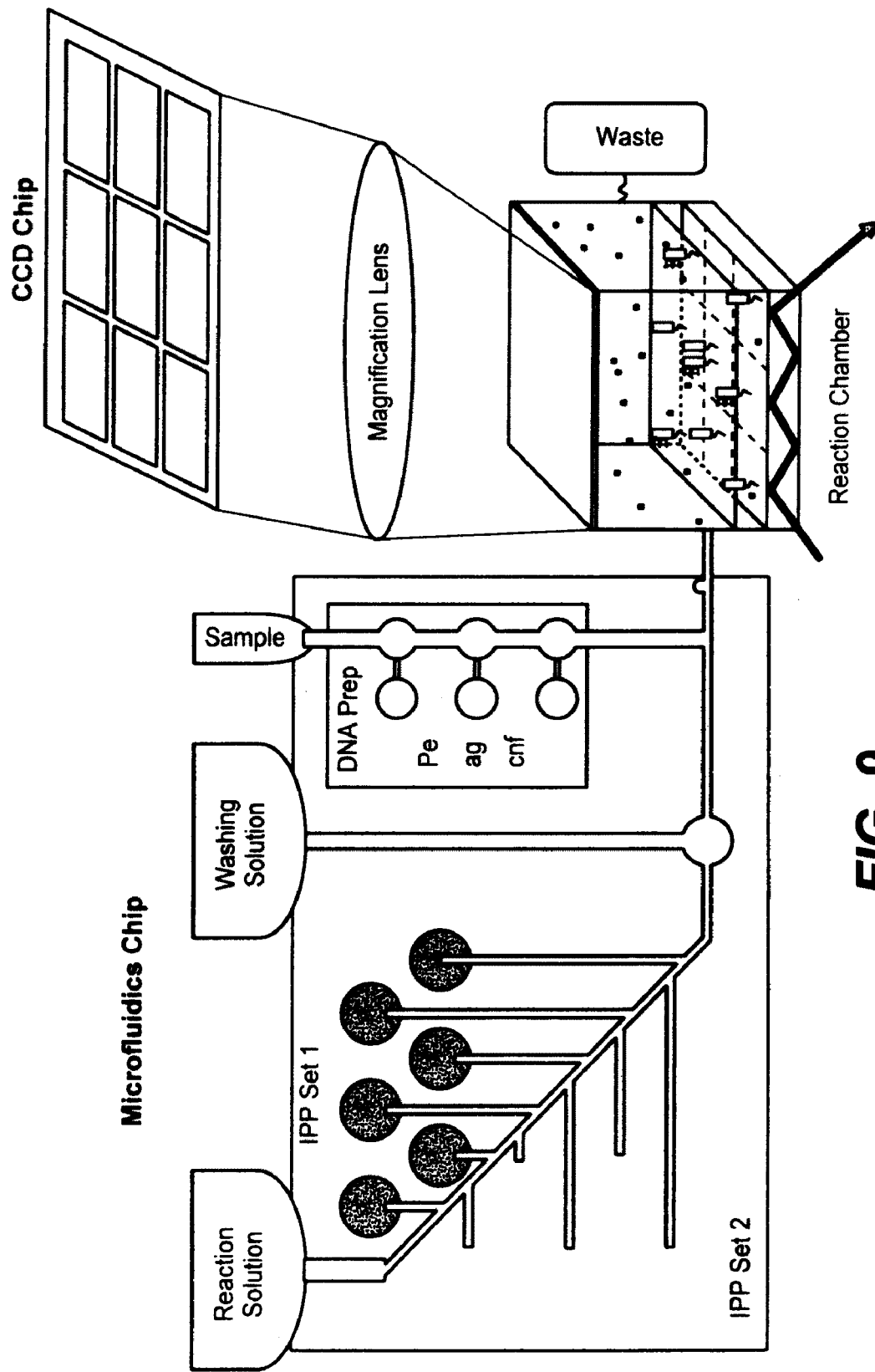

FIG. 9 depicts a schematic of a microfluidics device for the rSBH process. The device integrates DNA preparation, formation of random single molecule DNA arrays, combinatorial pool mixing, and cyclic loading and washing of the reaction chamber. When a sample tube is attached to the chip, a series of reactions is performed with pre-loaded reagents to isolate and fragment DNA, which is randomly attached to the array surface at a density of approximately one molecule per pixel. A microfluidics device is then used to mix two probe pools from 5' and 3' sets of informative probe pools (IPPs) with the reaction solution. One set of probe pools is labeled with a FRET donor, the other with a FRET acceptor. Mixed pools containing DNA ligase are then transferred to a reaction chamber above the single molecule DNA. Detectable ligation events occur when two probes (one from each pool) hybridize to adjacent complementary sequences of a target DNA molecule within a narrow zone of reflectance (~100 nm) above the array surface. Ligation of 5' and 3' probes within the zone of reflectance results in a FRET signal that is detected and scored by an ultra-sensitive CCD camera. After ligation events are scored, each pool mix is removed by a washing solution and a second pair of pools from the same sets of IPPs preloaded on the microfluidics chip is combined and introduced to the reaction chamber. By combining all possible pools within the two sets of IPPs, each target molecule in the array is scored for the presence/absence of every possible combination of probe sequences that exists within the two probe sets.

Figure 10:
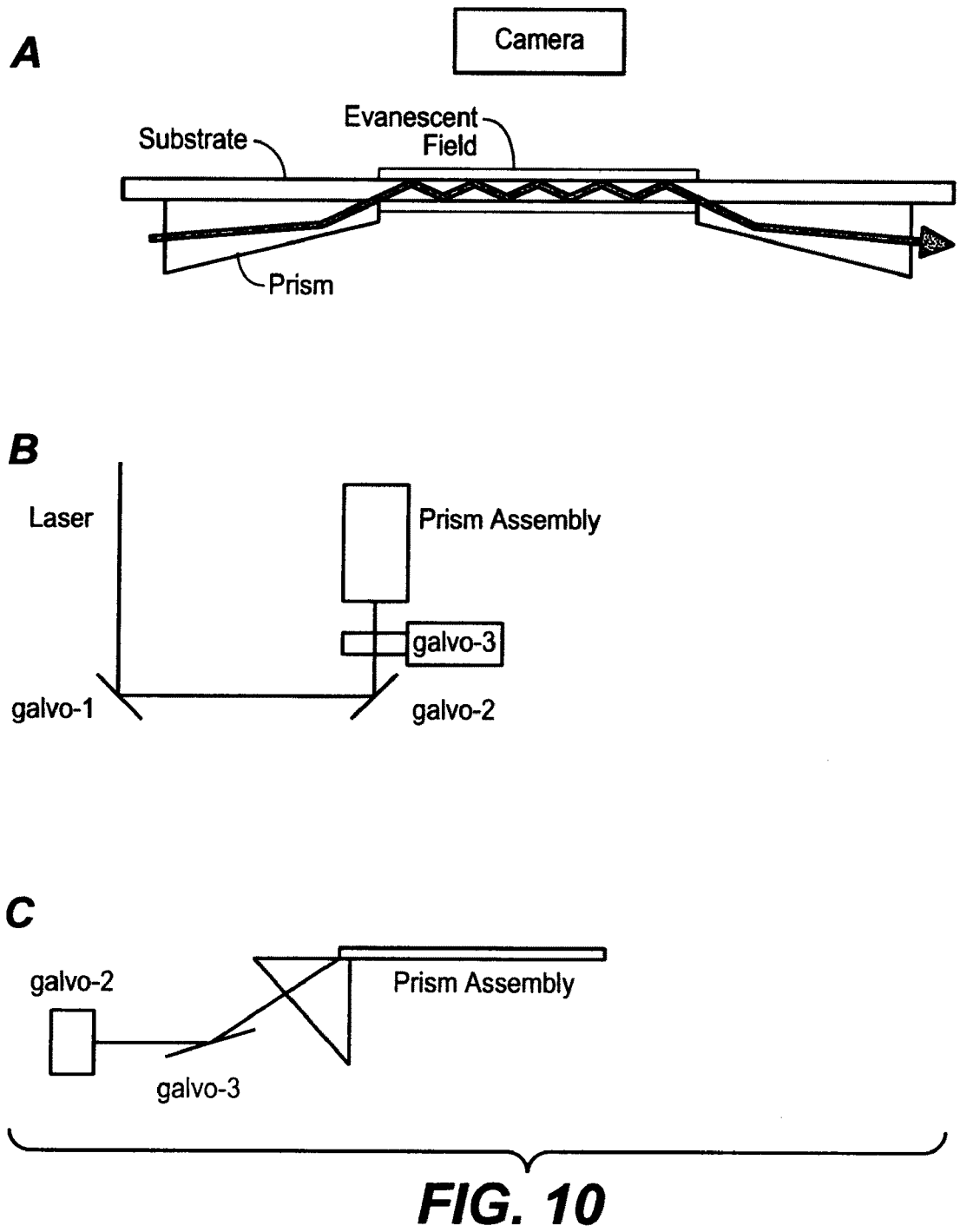

FIG. 10 depicts the basic optics and light path for the TIRM instrument. (a) Depiction of the traditional substrate positioned on top of the prisms and the light path that gives rise to an evanescent field. (b) and (c) show the use of galvanometers to control the light path from the laser to the prism assembly.

FIG. 11 depicts a schematic representation of rSBH components and processes showing the components of the rSBH instrument and stepwise description of the experimental process. Sample is collected and prepared (Steps 1 and 2) independent of the instrument. Resultant crude sample preparation is further processed for rSBH array formation (Step 3) by the sample integration module (Component A). Targets are subsequently arrayed on the substrate module within the reaction cartridge (Component B). Samples are subjected to SBH ligation assay (Step 4) using SBH probes delivered by the probe module (Component C). Resultant raw data is processed, resulting in assembly of sequence data (Step 5) and interpretive analysis (Step 6).

Figure 12:
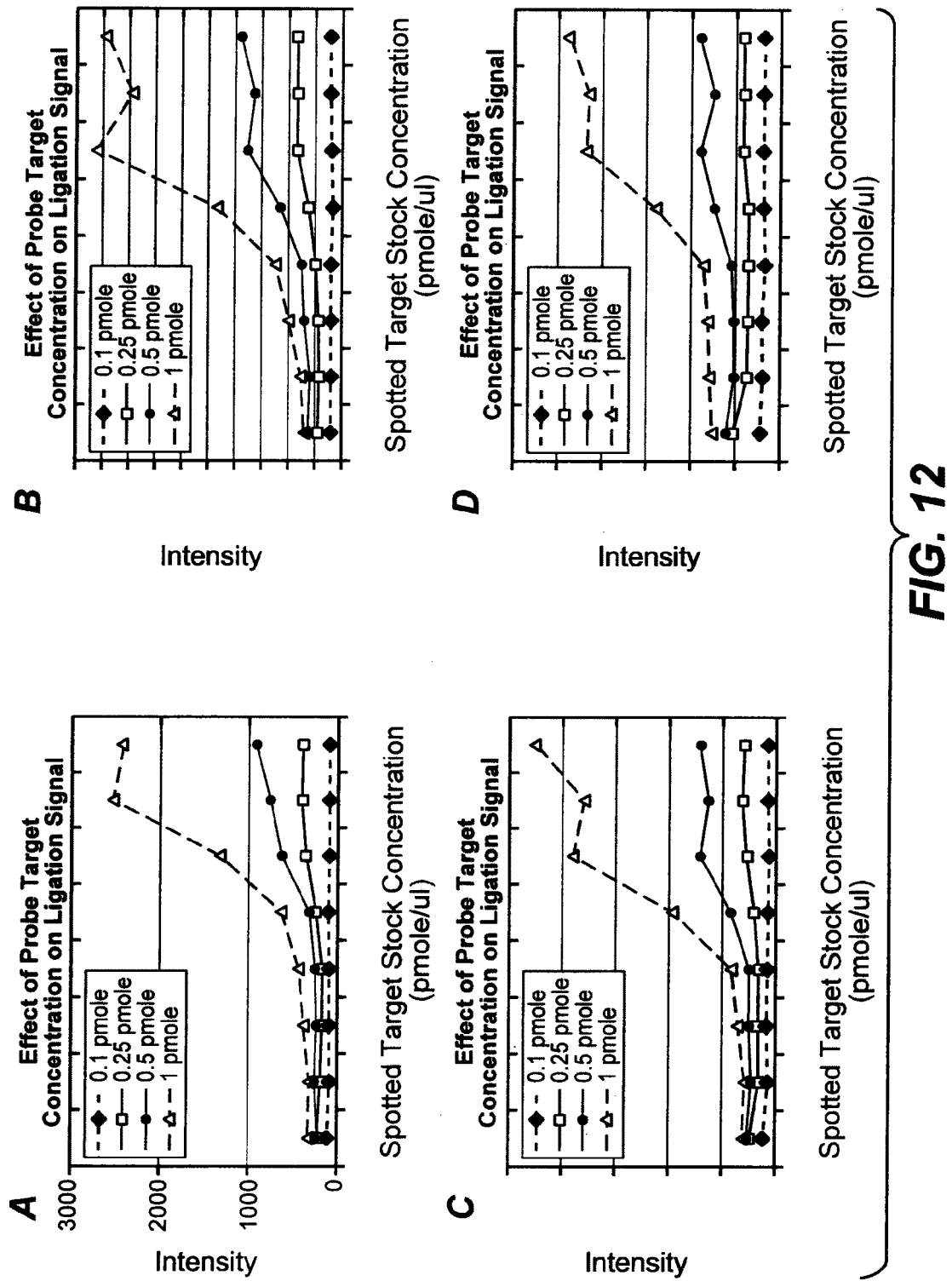

FIG. 12 shows the full-match ligation signal for 4 spotted targets. Four different targets were spotted at 7 different concentrations ranging from 1 to 90 µM. Ligation probe concentration (5' probe: 3' probe ratio is 1:1) were varied from 0.1 to 1 pmole/20 µl.

Figure 13:
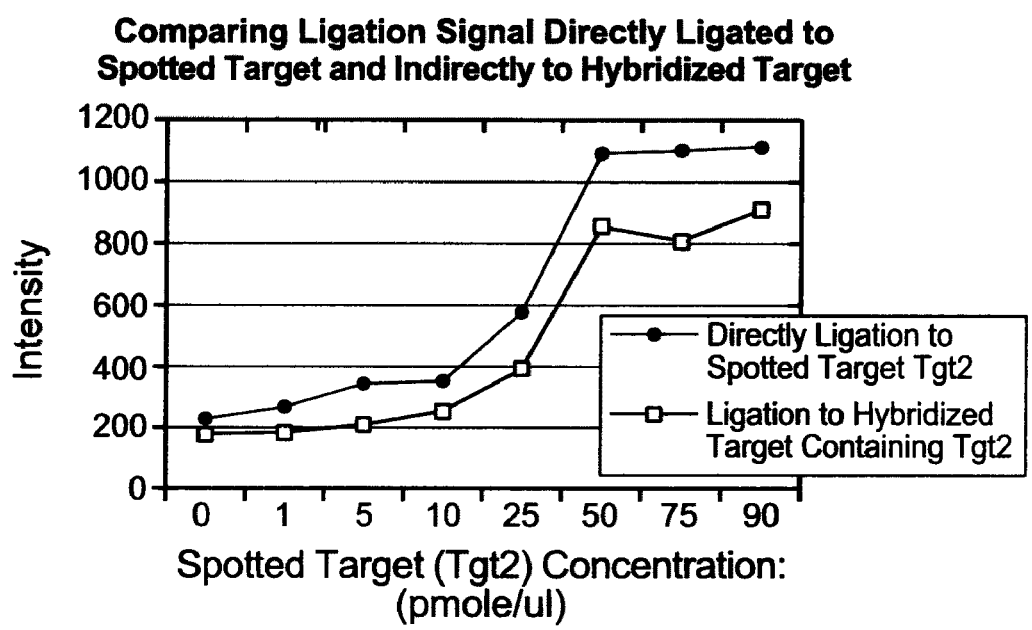

FIG. 13 shows a graphic representation of the spotted target serving as a capture probe for another target. The ligation signal was measured when the slide was directly hybridized/ ligated with Tg2-5' probe and Tgt2-3' probe (circles) and when the slide was pre-hybridized with target Tgt2-Tgt1-rc and then ligated with Tgt2-5' probe and Tgt2-3' probe (squares).

6. DETAILED DESCRIPTION OF THE PREFERRED EMBODIMENTS

The present invention provides single molecule DNA analysis methods and devices to rapidly and accurately sequence any long DNA fragment, mixture of fragments, entire genes, mixture of genes, mixtures of mRNAs, long segments of chromosomes, entire chromosomes, mixtures of chromosomes, entire genome, or mixtures of genomes. The method of the invention allows detection of pathogens present in complex biological samples at the single organism level and identification of virulence controlling genes. The method of the invention combines hybridization and especially sequencing by hybridization (SBH) technology with total internal reflection microscopy (TIRM) or other sensitive optical methods using fluorescence, nanoparticles, or electrical methods. The present invention also provides a sample arraying technology which creates virtual reaction chambers that are associated with individual pixels of an ultra-sensitive charge-coupled device (CCD) camera. Using informative pools of complete/universal sets of fluorescent-labeled oligonucleotide probes and combinatorial ligation process, arrayed genomes are repeatedly interrogated in order to decipher their sequences. Bioinformatics algorithms (co-owned, co-pending U.S. patent application Ser. No. 09/874,772; Drmanac et al., *Science* 260:1649-1652 (1993); Drmanac et al., *Nat. Biotech.* 16:54-58 (1998); Drmanac et al., "Sequencing and Fingerprinting DNA by Hybridization with Oligonucleotide Probes," In: *Encyclopedia of Analytical Chemistry*, pp. 5232-5237 (2000); Drmanac et al., "Sequencing by Hybridization (SBH): Advantages, Achievements, and Opportunities," In: *Advances in Biochemical Engineering/Biotechnology: Chip Technology*, Hoheisel, J. (Ed.), Vol. 76, pp. 75-98 (2002), all of which are herein incorporated by reference in their entirety) are used to transform informative fluorescent signals into assembled sequence data. The device can sequence over 100 mega bases of DNA per hour (30,000 bases/sec) using a single compact instrument located in a diagnostic laboratory or small mobile laboratory. Trace quantities of pathogen DNA can be detected, identified and sequenced within complex biological samples using the method of the present invention due to the large capacity of random single molecule arrays. Thus, random array SBH (rSBH) provides the necessary technology to allow DNA sequencing to play an important role in the defense against biowarfare agents, in addition to other sequencing applications.

The present invention provides a single DNA molecule analysis method to rapidly and accurately detect and identify any pathogen in complex biological mixtures of pathogen, host, and environmental DNA, and analyze any DNA in general, including individual human DNA. The method of the invention allows detection of pathogens present in the sample at the single organism level and identification of all virulence controlling genes. The method of the invention applies the process of combinatorial hybridization/ligation of small sets of universal informative probe pools (IPPs) to random single molecule arrays directly or after in situ amplification of individual arrayed molecules about 10- or 100-, or 1000- or 10,000-fold.

In a typical test, millions of randomly arrayed single DNA molecules obtained from a sample are hybridized with pairs of IPPs representing universal libraries of all possible probe sequences 8 to 10 bases in length. When two probes hybridize to adjacent complementary sequences in target DNAs, they are ligated to create a positive score for that target molecule and the accumulated set of such scores is compiled to assemble the target sequence from overlapping probe sequences.

In another embodiment of the present invention, the signature or sequence of individual targets can be used to assemble longer sequences of entire genes or genomes. In addition, by counting how many times the same molecule or segments from the same gene occur in the array, quantification of gene expression or pathogen DNA may be obtained and such data may be combined with the obtained sequences.

SBH is a well developed technology that may be practiced by a number of methods known to those skilled in the art. Specifically, the techniques related to sequencing by hybridization discussed in the following documents are incorporated by reference herein in their entirety: Bains and Smith, *J. Theor. Biol.* 135:303-307 (1988); Beaucage and Caruthers, *Tetrahedron Lett.* 22:1859-1862 (1981); Broude et al., *Proc. Natl. Acad. Sci. USA* 91:3072-3076 (1994); Breslauer et al., *Proc. Natl. Acad. Sci. USA* 83:3746-3750 (1986); Doty et al., *Proc. Natl. Acad. Sci. USA* 46:461-466 (1990); Chee et al., *Science* 274:610-614 (1996); Cheng et al., *Nat. Biotechnol.* 16:541-546 (1998); Dianzani et al., *Genomics* 11:48-53 (1991); PCT International Patent Application Serial No. WO 95/09248 to Drmanac; PCT International Patent Application Serial No. WO 96/17957 to Drmanac; PCT International Patent Application Serial No. WO 98/31836 to Drmanac; PCT International Patent Application Serial No. WO 99/09217 to Drmanac et al.; PCT International Patent Application Serial No. WO00/40758 to Drmanac et al.; PCT International Patent Application Serial No. WO 56937; co-owned, co-pending U.S. patent application Ser. No. 09/874,772 to Drmanac and Jin; Drmanac and Crkvenjakov, *Scientia Yugoslaviea* 16:99-107 (1990); Drmanac and Crkvenjakov, *Intl. J. Genome Res.* 1:59-79 (1992); Drmanac and Drmanac, *Meth. Enzymology* 303:165-178 (1999); Drmanac et al., U.S. Pat. No. 5,202,231; Drmanac et al., *Nucl. Acids Res.* 14:4691-4692 (1986); Drmanac et al., *Genomics* 4:114-128 (1989); Drmanac et al., *J. Biomol. Struct. Dyn.* 8:1085-1102 (1991); Drmanac et al., "Partial Sequencing by Hybridization: concept and Applications in Genome Analysis," in: *The First International Conference on Electrophoresis, Supercomputing and the Human Genome*, pp. 60-74, World Scientific, Singapore, Malaysia (1991); Drmanac et al., *Proceedings of the First Intl. Conf. Electrophoresis, Supercomputing and the Human Genome*, Cantor et al. eds, World Scientific Pub. Co., Singapore, 47-59 (1991); Drmanac et al., *Nucl. Acids Res.* 19:5839-5842 (1991); Drmanac et al., *Electrophoresis* 13:566-573 (1992); Drmanac et al., *Science* 260:1649-1652 (1993); Drmanac et al., *DNA and Cell Biol.* 9:527-534 (1994); Drmanac et al., *Genomics* 37:29-40 (1996); Drmanac et al., *Nature Biotechnology* 16:54-58 (1998); Gunderson et al., *Genome Res.* 8:1142-1153 (1998); Hacia et al., *Nature Genetics* 14:441-447 (1996); Hacia et al., *Genome Res.* 8:1245-1258 (1998); Hoheisel et al., *Mol. Gen.* 220:903-14: 125-132 (1991); Hoheisel et al., *Cell* 73:109-120 (1993); Holey et al., *Science* 147:1462-1465 (1965); Housby and Southern, *Nucl. Acids Res.* 26:4259-4266 (1998); Hunkapillar et al., *Science* 254:59-63 (1991); Khrapko, *FEBS Lett.* 256:118-122 (1989); Kozal et al., *Nature Medicine* 7:753-759 (1996); Labat and Drmanac, "Simulations of Ordering and Sequence Reconstruction of Random DNA Clones Hybridized with a Small Number of Oligomer Probes," in: *The Second International Conference on Electrophoresis, Supercomputing and the Human Genome*, pp. 555-565, World Scientific, Singapore, Malaysia (1992); Lehrach et al., *Genome Analysis: Genetic and Physical Mapping* 1:39-81 (1990), Cold Spring Harbor Laboratory Press; Lysov et al., *Dokl. Akad. Nauk. SSSR* 303:1508-1511 (1988); Lockhart et al., *Nat. Biotechnol.* 14:167501680 (1996); Maxam and Gilbert, *Proc. Natl. Acad. Sci. USA* 74:560-564 (1977); Meier et al, *Nucl. Acids Res.* 26:2216-2223 (1998); Michiels et al., *CABIOS* 3:203-210 (1987); Milosavljevic et al., *Genome Res.* 6:132-141 (1996); Milosavljevic et al., *Genomics* 37:77-86 (1996); Nikiforov et al., *Nucl. Acids Res.* 22:4167-4175 (1994); Pevzner and Lipschutz, "Towards DNA Sequencing Chips," in: *Mathematical Foundations of Computer Science* (1994); Poustka and Lehrach, *Trends Genet.* 2: 174-179 (1986); Privara et al., Eds., pp. 143-158, *The Proceedings of the 19th International Symposium, MFCS '94*, Kosice, Slovakia, Springer-Verlag, Berlin (1995); Saiki et al., *Proc. Natl. Acad. Sci. USA* 86:6230-6234 (1989); Sanger et al., *Proc. Natl. Acad. Sci. USA* 74:5463-5467 (1977); Scholler et al., *Nucl. Acids Res.* 23:3842-3849 (1995); PCT International Application Serial No. WO 89/10977 to Southern; U.S. Pat. No. 5,700,637 to Southern; Southern et al., *Genomics* 13:1008-1017 (1992); Strezoska et al., *Proc. Natl. Acad. Sci. USA* 88:10089-10093 (1991); Sugimoto et al., *Nucl. Acid Res.* 24:4501-4505 (1996); Wallace et al., *Nucl. Acids Res.* 6:3543-3557 (1979); Wang et al., *Science* 280:1077-1082 (1998); Wetmur, *Crit. Rev. Biochem. Mol. Biol.* 26:227-259 (1991).

Advantages of rSBH:

rSBH minimizes or eliminates target-target blocking interactions between two target DNA molecules that are attached at an appropriate distance. The low complexity of DNA sequence (between 200-2000 bases) per spot reduces the likelihood of inverse repeats that can block each other. Palindromes and hairpin arms are separated in some fragments with one cut per every 20 bases of source DNA on average and attach to non-complementary primer DNA. False positives are minimized because overlapped fragments have different repeated and/or strong mismatch sequences. Probe-probe ligation products are removable by washing. The combination of hybridization/ligation specificity and differential full-match/mismatch stability for the 11-13-mer probes made by ligation has the potential for producing more accurate data. rSBH provides an efficient method of using three-probe ligation in solution, including analysis of short DNA. Pools of patterned probes can be efficiently used on both probe components to provide more informative data. Another advantage is that very low amounts of source DNA are required. The need for standard probe-spot array preparation is eliminated, thereby reducing cost. rSBH provides for multiplex sequencing of up to 1000 samples tagged with different primers or adapters. In addition, the invention provides for detection of a single variant in a pool of up to one million individual samples. Heterozygotes can be detected by counting two variants. The invention provides for 10- to 100,000-fold more information per surface than the standard arrays.

6.1 Preparation and Labeling of Polynucleotides

The practice of the instant invention employs a variety of polynucleotides. Typically some of the polynucleotides are detectably labeled. Species of polynucleotides used in the practice of the invention include target nucleic acids and probes.

The term "probe" refers to a relatively short polynucleotide, preferably DNA. Probes are preferably shorter than the target nucleic acid by at least one base, and more preferably they are 25 bases or fewer in length, still more preferably 20 bases or fewer in length. Of course, the optimal length of a probe will depend on the length of the target nucleic acid being analyzed. In de novo sequencing (no reference sequence used) for a target nucleic acid composed of about 100 or fewer bases, the probes are preferably at least 7-mers; for a target nucleic acid of about 100-200 bases, the probes are preferably at least 8-mers; for a target nucleic acid of about 200-400 bases, the probes are preferably at least 9-mers; for a target nucleic acid of about 400-800 bases, the probes are preferably at least 10-mers; for a target nucleic acid of about 800-1600 bases, the probes are at least 11-mers; for a target nucleic acid of about 1600-3200 bases, the probes are preferably at least 12-mers; for a target nucleic acid of about 3200-6400 bases, the probes are preferably at least 13-mers; and for a target nucleic acid of about 6400-12,800 bases, the probes are preferably at least 14-mers. For every additional two-fold increase in the length of the target nucleic acid, the optimal probe length is one additional base.

Those of skill in the art will recognize that for SBH applications utilizing ligated probes, the above-delineated probe lengths are post-ligation. Probes are normally single stranded, although double-stranded probes may be used in some applications.

While typically the probes will be composed of naturally-occurring bases and native phosphodiester backbones, they need not be. For example, the probes may be composed of one or more modified bases, such as 7-deazaguanosine or the universal "M" base, or one or more modified backbone interlinkages, such as a phosphorothioate. The only requirement is that the probes be able to hybridize to the target nucleic acid. A wide variety of modified bases and backbone interlinkages that can be used in conjunction with the present invention are known, and will be apparent to those of skill in the art.

The length of the probes described above refers to the length of the informational content of the probes, not necessarily the actual physical length of the probes. The probes used in SBH frequently contain degenerate ends that do not contribute to the information content of the probes. For example, SBH applications frequently use mixtures of probes of the formula $N_xB_yN_z$, wherein N represents any of the four bases and varies for the polynucleotides in a given mixture, B represents any of the four bases but is the same for each of the polynucleotides in a given mixture, and x, y, and z are integers. Typically, x and z are independent integers between 0 and 5 and y is an integer between 4 and 20. The number of known bases By defines the "information content" of the polynucleotide, since the degenerate ends do not contribute to the information content of the probes. Linear arrays comprising such mixtures of immobilized polynucleotides are useful in, for example, sequencing by hybridization. Hybridization discrimination of mismatches in these degenerate probe mixtures refers only to the length of the informational content, not the full physical length.

Probes for use in the instant invention may be prepared by techniques well known in the art, for example by automated synthesis using an Applied Biosystems synthesizer. Alternatively, probes may be prepared using Genosys Biotechnologies Inc. methods using stacks of porous Teflon wafers. For purposes of this invention, the source of oligonucleotide probes used is not critical, and one skilled in the art will recognize that oligonucleotides prepared using other methods currently known or later developed will also suffice.

The term "target nucleic acid" refers to a polynucleotide, or some portion of a polynucleotide, for which sequence information is desired, typically the polynucleotide that is sequenced in the SBH assay. The target nucleic acid can be any number of nucleotides in length, depending on the length of the probes, but is typically on the order of 100, 200, 400, 800, 1600, 3200, 6400, or even more nucleotides in length. A sample typically may have more than 100, more than 1000, more than 10,000, more than 100,000, more than one million, or more than 10 million targets. The target nucleic acid may be composed of ribonucleotides, deoxyribonucleotides, or mixtures thereof. Typically, the target nucleic acid is a DNA. While the target nucleic acid can be double-stranded, it is preferably single stranded. Moreover, the target nucleic acid can be obtained from virtually any source. Depending on its length, it is preferably sheared into fragments of the above-delineated sizes prior to using an SBH assay. Like the probes, the target nucleic acid can be composed of one or more modified bases or backbone interlinkages.

The target nucleic acid may be obtained from any appropriate source, such as cDNAs, genomic DNA, chromosomal DNA, microdissected chromosomal bands, cosmid or yeast artificial chromosome (YAC) inserts, and RNA, including mRNA without any amplification steps. For example, Sambrook et al. *Molecular Cloning: A Laboratory Manual*, Cold Spring Harbor Press, NY (1989), herein incorporated by reference in its entirety, describes three protocols for the isolation of high molecular weight DNA from mammalian cells (p. 9.14-9.23).

The polynucleotides would then typically be fragmented by any of the methods known to those of skill in the art including, for example, using restriction enzymes as described at 9.24-9.28 of Sambrook et al. (1989), shearing by ultrasound, and NaOH treatment. A particularly suitable method for fragmenting DNA utilizes the two base recognition endonuclease, CviJI, described by Fitzgerald et al., *Nucl. Acids Res.* 20:3753-3762 (1992), incorporated herein by reference in its entirety.

In a preferred embodiment, the target nucleic acids are prepared so that they cannot be ligated to each other, for example by treating the fragmented nucleic acids obtained by enzyme digestion or physical shearing with a phosphatase (i.e. calf intestinal phosphatase). Alternatively, nonligatable fragments of the sample nucleic acid may be obtained by using random primers (i.e. $N_5$-$N_9$, wherein N=A, G, T, or C), which have no phosphate at their 5'-ends, in a Sanger-dideoxy sequencing reaction with the sample nucleic acid.

In most cases it is important to denature the DNA to yield single stranded pieces available for hybridization. This may be achieved by incubating the DNA solution for 2-5 minutes at 80-90° C. The solution is then cooled quickly to 2° C. to prevent renaturation of the DNA fragments before they are contacted with the probes.

Probes and/or target nucleic acids may be detectably labeled. Virtually any label that produces a detectable signal and that is capable of being immobilized on a substrate or attached to a polynucleotide can be used in conjunction with the arrays of the invention. Preferably, the signal produced is amenable to quantification. Suitable labels include, by way of example and not limitation, radioisotopes, fluorophores, chromophores, chemiluminescent moieties, etc.

Due to their ease of detection, polynucleotides labeled with fluorophores are preferred. Fluorophores suitable for labeling polynucleotides are described, for example, in the Molecular Probes catalog (Molecular Probes, Inc., Eugene, Oreg.), and the references cited therein. Methods for attaching fluorophore labels to polynucleotides are well known, and can be found, for example, in Goodchild, *Bioconjug. Chem.* 1:165-187 (1990), herein incorporated by reference in its entirety. A preferred fluorophore label is Cy5 dye, which is available from Amersham Biosciences.

Alternatively, the probes or targets may be labeled by any other technique known in the art. Preferred techniques include direct chemical labeling methods and enzymatic labeling methods, such as kinasing and nick-translation. Labeled probes could readily be purchased from a variety of commercial sources, including GENSET, rather than synthesized.

In general, the label can be attached to any part of the probe or target polynucleotide, including the free terminus of one or more of the bases. In preferred embodiments, the label is attached to a terminus of the polynucleotide. The label, when attached to a solid support by means of a polynucleotide, must be located such that it can be released from the solid support by cleavage with a mismatch-specific endonuclease, as described in co-owned, co-pending U.S. patent application Ser. No. 09/825,408 (herein incorporated by reference in its entirety). Preferably, the position of the label will not interfere with hybridization, ligation, cleavage or other post-hybridization modifications of the labeled polynucleotide.

Some embodiments of the invention employ multiplexing, i.e. the use of a plurality of distinguishable labels (such as different fluorophores). Multiplexing allows the simultaneous detection of a plurality of sequences in one hybridization reaction. For example, a multiplex of four colors reduces the number of hybridizations required by an additional factor of four.

Other embodiments employ the use of informative pools of probes to reduce the redundancy normally found in SBH protocols, thereby reducing the number of hybridization reactions needed to unambiguously determine a target DNA sequence. Informative pools of probes and methods of using the same can be found in co-owned, co-pending U.S. patent application Ser. No. 09/479,608, which is incorporated herein by reference in its entirety.

6.2 Attachment of Polynucleotides to a Solid Substrate

Some embodiments of the instant invention require polynucleotides, for example target DNA fragments, to be attached to a solid substrate. In preferred embodiments, the appropriate DNA samples are detectably labeled and randomly attached to a solid substrate at a concentration of 1 fragment per pixel.

The nature and geometry of the solid substrate will depend upon a variety of factors, including, among others, the type of array and the mode of attachment (i.e. covalent or non-covalent). Generally, the substrate can be composed of any material which will permit immobilization of the polynucleotide and which will not melt or otherwise substantially degrade under the conditions used to hybridize and/or denature nucleic acids. In addition, where covalent immobilization is contemplated, the substrate should be activatable with reactive groups capable of forming a covalent bond with the polynucleotide to be immobilized.

A number of materials suitable for use as substrates in the instant invention have been described in the art. In preferred embodiments, the substrate is made of an optically clear substance, such as glass slides. Other exemplary suitable materials include, for example, acrylic, styrene-methyl methacrylate copolymers, ethylene/acrylic acid, acrylonitrile-butadiene-styrene (ABS), ABS/polycarbonate, ABS/polysulfone, ABS/polyvinyl chloride, ethylene propylene, ethylene vinyl acetate (EVA), nitrocellulose, nylons (including nylon 6, nylon 6/6, nylon 6/6-6, nylon 6/10, nylon 6/12, nylon 11, and nylon 12), polycarylonitrile (PAN), polyacrylate, polycarbonate, polybutylene terephthalate (PBT), polyethylene terephthalate (PET), polyethylene (including low density, linear low density, high density, cross-linked and ultra-high molecular weight grades), polypropylene homopolymer, polypropylene copolymers, polystyrene (including general purpose and high impact grades), polytetrafluoroethylene (PTFE), fluorinated ethylene-propylene (FEP), ethylene-tetrafluoroethylene (ETFE), perfluoroalkoxyethylene (PFA), polyvinyl fluoride (PVF), polyvinylidene fluoride (PVDF), polychlorotrifluoroethylene (PCTFE), polyethylene-chlorotrifluoroethylene (ECTFE), polyvinyl alcohol (PVA), silicon styrene-acrylonitrile (SAN), styrene maleic anhydride (SMA), metal oxides and glass.

In general, polynucleotide fragments may be bound to a support through appropriate reactive groups. Such groups are well known in the art and include, for example, amino (—NH$_2$), hydroxyl (—OH), or carboxyl (—COOH) groups. Support-bound polynucleotide fragments may be prepared by any of the methods known to those of skill in the art using any suitable support such as glass. Immobilization can be achieved by many methods, including, for example, using passive adsorption (Inouye and Hondo, *J. Clin. Microbiol.* 28:1469-1472 (1990), herein incorporated by reference in its entirety), using UV light (Dahlen et al., *Mol. Cell Probes* 1:159-168 (1987), herein incorporated by reference in its entirety), or by covalent binding of base-modified DNA (Keller, et al., *Anal. Biochem.* 170:441-451 (1988), Keller et al., *Anal. Biochem.* 177:392-395 (1989), both of which are herein incorporated by reference in their entirety), or by formation of amide groups between the probe and the support (Zhang et al., *Nucl. Acids Res.* 19:3929-3933 (1991), herein incorporated by reference in its entirety).

It is contemplated that a further suitable method for use with the present invention is that described in PCT Patent Application WO 90/03382 (to Southern et al.), incorporated herein by reference. This method of preparing a polynucleotide fragment bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

Alternatively, addressable-laser-activated photodeprotection may be employed in the chemical synthesis of oligonucleotides directly on a glass surface, as described by Fodor et al., *Science* 251:767-773 (1991), incorporated herein by reference.

One particular way to prepare support-bound polynucleotide fragments is to utilize the light-generated synthesis described by Pease et al., *Proc. Natl. Acad. Sci. USA* 91:5022-5026 (1994), incorporated herein by reference. These authors used current photolithographic techniques to generate arrays of immobilized oligonucleotide probes, i.e. DNA chips. These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner and then used in SBH sequencing, as described herein.

In a preferred embodiment, the DNA fragments of the invention are connected to the solid substrate by means of a linker moiety. The linker may be comprised of atoms capable of forming at least two covalent bonds, such as carbon, silicon, oxygen, sulfur, phosphorous, and the like, or may be comprised of molecules capable of forming at least two covalent bonds, such as sugar-phosphate groups, amino acids, peptides, nucleosides, nucleotides, sugars, carbohydrates, aromatic rings, hydrocarbon rings, linear and branched hydrocarbons, and the like. In a particularly preferred embodiment of the invention, the linker moiety is composed of alkylene glycol moieties. In preferred embodiments, a detectable label is attached to the DNA fragment (i.e. target DNA).

6.3 Formation of Detectably Labeled Duplexes on a Solid Support

In one preferred embodiment of the invention, a labeled probe is bound by means of complementary base-pairing interactions to a detectably labeled target nucleic acid that is itself attached to a solid substrate as part of a polynucleotide array, thereby forming a duplex. In another preferred embodiment, a labeled probe is covalently attached, i.e. ligated, to another probe that is bound by means of complementary base-pairing interactions to a target nucleic acid that is itself attached to a solid substrate as part of a spatially-addressable polynucleotide array, if the two probes hybridize to a target nucleic acid in a contiguous fashion.

As used herein, nucleotide bases "match" or are "complementary" if they form a stable duplex or binding pair under specified conditions. The specificity of one base for another is dictated by the availability and orientation of hydrogen bond donors and acceptors on the bases. For example, under conditions commonly employed in hybridization assays, adenine ("A") matches thymine ("T"), but not guanine ("G") or cytosine ("C"). Similarly, G matches C, but not A or T. Other bases which interact in less specific fashion, such as inosine or the Universal Base ("M" base, Nichols et al., *Nature* 369: 492-493 (1994), herein incorporated by reference in its entirety), or other modified bases, for example methylated bases, are complementary to those bases for which they form a stable duplex under specified conditions. Nucleotide bases which are not complementary to one another are termed "mismatches."

A pair of polynucleotides, e.g. a probe and a target nucleic acid, are termed "complementary" or a "match" if, under specified conditions, the nucleic acids hybridize to one another in an interaction mediated by the pairing of complementary nucleotide bases, thereby forming a duplex. A duplex formed between two polynucleotides may include one or more base mismatches. Such a duplex is termed a "mismatched duplex" or heteroduplex. The less stringent the hybridization conditions are, the more likely it is that mismatches will be tolerated and relatively stable mismatched duplexes can be formed.

A subset of matched polynucleotides, termed "perfectly complementary" or "perfectly matched" polynucleotides, is composed of pairs of polynucleotides containing continuous sequences of bases that are complementary to one another and wherein there are no mismatches (i.e. absent any surrounding sequence effects, the duplex formed has the maximal binding energy for the particular nucleic acid sequences). "Perfectly complementary" and "perfect match" are also meant to encompass polynucleotides and duplexes which have analogs or modified nucleotides. A "perfect match" for an analog or modified nucleotide is judged according to a "perfect match rule" selected for that analog or modified nucleotide (e.g. the binding pair that has maximal binding energy for a particular analog or modified nucleotide).

In the case where a pool of probes with degenerate ends of the type $N_x B_y N_z$ is used, as described above, a perfect match encompasses any duplex where the information content regions, i.e. the $B_y$ regions, of the probes are perfectly matched. Discrimination against mismatches in the N regions will not affect the results of a hybridization experiment, since such mismatches do not interfere with the information derived from the experiment.

In a particularly preferred embodiment of the invention, a polynucleotide array is provided wherein target DNA fragments are provided on a solid substrate under conditions which permit them to hybridize with at least one set of detectably labeled oligonucleotide probes provided in solution. Both within the sets and between the sets the probes may be of the same length or of different lengths. Guidelines for determining appropriate hybridization conditions can be found in papers such as Drmanac et al., (1990), Khrapko et al. (1991), Broude et al., (1994) (all cited supra) and WO 98/31836, which is incorporated herein by reference in its entirety. These articles teach the ranges of hybridization temperatures, buffers, and washing steps that are appropriate for use in the initial steps of SBH. The probe sets may be applied to the target nucleic acid separately or simultaneously.

Probes that hybridize to contiguous sites on the target nucleic acid are covalently attached to one another, or ligated. Ligation may be implemented by a chemical ligating agent (e.g. water-soluble carbodiimide or cyanogen bromide), by a ligase enzyme, such as the commercially available $T_4$ DNA ligase, by stacking interactions, or by any other means of causing chemical bond formation between the adjacent probes. Guidelines for determining appropriate conditions for ligation can be found in papers such as co-owned U.S. patent application Ser. Nos. 09/458,900, 09/479,608, and 10/738,108, all of which are herein incorporated by reference in their entirety.

6.4 Random Array SBH (rSBH)

The method of the present invention uses random array SBH (rSBH) which extends the combinatorial ligation process to single molecule arrays, greatly increasing the sensitivity and power of the method of the invention. rSBH relies on successive interrogations of randomly arrayed DNA fragments by informative pools of labeled oligonucleotides. In the method of the present invention, complex DNA mixtures to be sequenced are displayed on an optically clear surface within the focal plane of a total internal fluorescence reflection microscopy (TIRM) platform and continuously monitored using an ultra-sensitive mega pixel CCD camera. DNA fragments are arranged at a concentration of approximately 1 to 3 molecules per square micron, an area corresponding to a single CCD pixel. TIRM is used to visualize focal and close contacts between the object being studied and the surface to which it is attached. In TIRM, the evanescent field from an internally reflected excitation source selectively excites fluorescent molecules at or near a surface, resulting in very low background scattered light and good signal-to-background contrast. The background and its associated noise can be made low enough to detect single fluorescent molecules under ambient conditions. (see Abney et al. *Biophys. J.* 61:542-552 (1992); Ambrose et al., *Cytometry* 36:224-231 (1999); Axelrod, *Traffic* 2:764-774 (2001); Fang and Tan, "Single Molecule Imaging and Interaction Study Using Evanescent Wave Excitation," *American Biotechnology Laboratory (ABL) Application Note*, April 2000; Kawano and Enders, "Total Internal Reflection Fluorescence Microscopy," *American Biotechnology Laboratory Application (ABL) Application Note*, December 1999; Reichert and Truskey, *J. Cell Sci.* 96 (Pt. 2):219-230 (1990), all of which are herein incorporated by reference in their entirety).

Using microfluidic technology, pairs of probe pools labeled with donor and acceptor fluorophores are mixed with DNA ligase and presented to the random array. When probes hybridize to adjacent sites on a target fragment, they are ligated together generating a fluorescence resonance energy transfer (FRET) signal. FRET is a distance-dependent (between 10-100 Å) interaction between the electronic excited states of two fluorescent molecules in which excitation is transferred from a donor molecule to an acceptor molecule without emission of a photon (Didenko, *Biotechniques* 31:1106-1121 (2001); Ha, *Methods* 25:78-86 (2001); Klostermeier and Millar, *Biopolymers* 61:159-179 (2001-2002), all of which are herein incorporated by reference in their entirety). These signals are detected by the CCD camera indicating a matching sequence string within that fragment. Once the signals from the first pool are detected, probes are removed and successive cycles are used to test different probe combinations. The entire sequence of each DNA fragment is compiled based on fluorescent signals generated by hundreds of independent hybridization/ligation events.

Although only one detectable color will suffice, multiple colors will increase multiplexing of the combinatorics and improve the efficiency of the system. The current state of the art suggests that four colors can be used simultaneously. In addition to traditional direct fluorescence strategies, FRET-based systems, time-resolved systems and time-resolved FRET signaling systems will also be used (Didenko, *Biotechniques* 31:1106-1121 (2001), herein incorporated by reference in its entirety). New custom chemistries, such as quantum dot enhanced triple FRET systems may also be used. Overcoming a weak signal may be overcome using dendramer technologies and related signal amplification technologies.

Unlike traditional hybridization processes, the method of the present invention relies on a synergistic interaction of hybridization and ligation, in which short probes from two pools are ligated together to generate longer probes with far more informational power. For example, two sets of 1024 five-mer oligonucleotides can be combined to detect over a million possible 10-mer sequence strings. The use of informative probe pools (in which all probes share a common label) greatly simplifies the process, allowing millions of potential probe pairings to occur with only a few hundred pool combinations. Multiple overlapping probes reading consecutive bases allow an accurate determination of DNA sequence from the obtained hybridization pattern. The combinatorial ligation and informative pools technologies described above are augmented by extending their use to single molecule sequencing.

6.5 Structured Random DNA Preparation

A. DNA Isolation and Initial Fragmentation

Cells are lysed and DNA is isolated using basic well-established protocols (Sambrook et al., supra, 1999; Current Protocols in Molecular Biology, Ausubel et al., eds. John Wiley and Sons, Inc., NY, 1999, both of which are herein incorporated by reference in their entirety) or commercial kits [e.g. those available from QIAGEN (Valencia, Calif.) or Promega (Madison, Wis.)]. Critical requirements are: 1) the DNA is free of DNA processing enzymes and contaminating salts; 2) the entire genome is equally represented; and 3) the DNA fragments are between ~5,000 and ~100,000 bp in length. No digestion of the DNA is required because shear forces created during lysis and extraction will give rise to fragments in the desired range. In another embodiment, shorter fragments (1-5 kb) can be generated by enzymatic fragmentation. The input genome number of 10-100 copies will ensure overlap of the entire genome and tolerates poor capture of targets on the array. A further embodiment provides for carrier, circular synthetic double-stranded DNA to be used in the case of small amounts of DNA.

B. DNA Normalization

In some embodiments, normalization of environmental samples may be necessary to reduce the DNA contribution of prevalent species to maximize the total number of distinct species that are sequenced per array. Because rSBH requires as few as 10 genome equivalents, a thorough DNA normalization or subtraction process can be implemented. Normalization can be accomplished using commonly utilized methods used for normalizing cDNA libraries during their production. DNA collected from the sample is divided in two, with one being of ten-fold greater mass than the other. The sample of greater quantity is biotinylated by terminal transferase and ddCTP and attached as a single stranded DNA to a streptavidin column or streptavidin-coated beads. Alternatively, biotinylated random primers may be employed to generate sequence for attachment to streptavidin. Whole genome amplification methodologies (Molecular Staging, Inc., New Haven, Conn.) can also be applied. The sample to be normalized is then hybridized to the attached molecules and those molecules that are over-represented in the sample are preferentially removed from the solution due to the greater number of binding sites. Several hybridization/removal cycles can be applied on the same sample to achieve full normalization. Another embodiment provides for efficient hybridization of long double-stranded DNA fragments without DNA denaturation by generating short terminal regions of single-stranded DNA with a timed lambda exonuclease digestion.

Further embodiments provide for sequencing low abundance members that are difficult to analyze by combining DNA normalization and rSBH. Normalization of one sample against another allows monitoring of changes in community structure and identifying new members as conditions change.

C. Secondary DNA Fragmentation and Adapter Attachment

The present invention provides for long DNA fragments generated by shear forces to be suspended in solution within a chamber located on the glass slide. The concentration of the DNA is adjusted such that the volume occupied by each fragment is in the order of 50×50×50 µm. The reaction chamber comprises a mix of restriction enzymes, T4 DNA ligase, a strand displacing polymerase, and specially designed adapters. Partial digestion of the DNA by the restriction enzymes yields fragments with an average length of 250 bp with uniform overhang sequences. T4 DNA ligase joins non-phosphorylated double-stranded adapters to the ends of the genomic fragments via complementary sticky-ends resulting in a stable structure of genomic insert with one adapter at each end, but with a nick in one of the strands where the ligase was unable to catalyze the formation of the phosphodiester bond (FIG. 1). T4 DNA ligase is active in most restriction enzyme buffers but requires the addition of ATP and a molar excess of adapters relative to genomic DNA to promote the ligation of adapters at each end of the genomic molecule. Using non-phosphorylated adapters is important to prevent adapter-adapter ligation. Additionally, the adapters contain two primer-binding sites and are held in a hairpin structure by cross-linked bases at the hairpin end that prevents dissociation of the adapters during melting at elevated temperatures. Extension from the 3'-ends with a strand-displacing polymerase such as Vent or Bst results in the production of a DNA strand with adapter sequences at both ends. However, at one end the adapter will be maintained in the hairpin structure that is useful to prevent association of complementary sequences on the other end of the DNA fragment.

The invention provides for random DNA arrays to sequence multiples of highly similar samples (i.e. individual DNA from patients) in one assay by tagging DNA fragments of each sample prior to random array formation. One or both adapters used for incorporation of primer sequences at the end of the DNA fragments can have a tag cassette. A different tag cassette can be used for each sample. After attaching adapters (preferably by ligation), DNA of all samples is mixed and single random array is formed. After sequencing of fragments is completed, fragments that belong to each sample are recognized by the assigned tag sequence. Use of the tag approach allows efficient sequencing of a smaller number of targeted DNA regions from about 10-1000 samples on high capacity random arrays having up to about 10 million DNA fragments.

D. DNA Attachment and In Situ Amplification

The adapter-linked genomic DNA is then localized with other fragments from the original 5-100 kb fragment onto the glass slide by hybridization to an oligonucleotide that is complementary to the adapter sequences (primer B). After adapter ligation and DNA extension, the solution is heated to denature the molecules which, when in contact with a high concentration of primer oligonucleotides attached to the surface of the slide, hybridizes to these complementary sequences during the re-annealing phase. In an alternative embodiment, in situ amplification does not occur and the adapter is attached to the support and the DNA fragments are ligated. Most of the DNA structures that arise from the one parent molecule are localized to one section of the slide in the order of 50×50 µm; therefore if 1000 molecules are generated from the restriction digest of one parent molecule, each fragment will occupy, on average, a 1-4 µm$^2$ region. Such 1-4 µm$^2$ region can be observed by a single pixel of a CCD camera and represents a virtual reaction well within an array of one million wells.

Lateral diffusion of DNA fragments more than 50 µm across the slide surface is unlikely to be significant in the short period of time in a 50-100 µm thick capillary chamber that prevents liquid turbulence. In addition, high viscosity buffers or gel can be used to minimize diffusion. In yet a further embodiment, limited turbulence is needed to spread hundreds of short DNA fragments derived from single 5-100 kb molecules over a 50×50 µm surface. Note that the spreading does not have to be perfect because SBH can analyze mixtures of a few DNA fragments at the same pixel location. A few fractions of the original sample with more uniform fragment length (i.e. 5-10 kb, 10-20 kb, 20-40 kb, 40-1000 kb) may be prepared to achieve equal spacing between short fragments. Furthermore, an electric field can be used to pool short DNA fragments to the surface for attachment. Partially structured arrays with local mixing of short fragments are almost as efficient as fully structured arrays because no short fragments from any single, long fragment is mixed with short fragments generated from about 10,000 other long initial fragments.

A further embodiment of the invention provides for a ligation process that attaches two primer sequences to DNA fragments. This approach is based on targeting single stranded DNA produced by denaturation of double-stranded DNA fragments. Because single-stranded DNA has unique 5' and 3' ends, specific primer sequences can be attached to each end. Two specific adapters, each comprising two oligonucleotides, are designed (see FIG. 2) that have specifically modified ends, wherein F and B represent unbound, solution-free primer (F) and surface-bound (B) primer sequences and f and b represent sequences complementary to these primer sequences (i.e. primer f is complementary to primer F). The only 3'-OH group that is necessary for ligation to the DNA fragment is on primer F, the other oligonucleotides can have a dideoxy 3' end (dd) to prevent adapter-adapter ligation. In addition to the 5'-phosphate group (P) present on primer b, primer B may also have a 5'-P group to be used for degradation of this primer after adapter ligation to expose primer b sequence for hybridization to the surface-attached primer/capture probe B. To allow for adapter ligation to any DNA fragment generated from the source DNA by random fragmentation, the oligonucleotides f and B have several (approximately 3-9, preferably 5-7) degenerate bases (Ns).

Although rSBH detection is designed for single molecule detection, some embodiments amplify each DNA target in situ. The method of the invention provides for isothermal, exponential amplification within a micron-sized spot of localized amplicon, herein denoted as "ampliot" (defined to be an amplicon spot) (FIG. 3). The amplification is achieved by use of a primer bound to the surface (primer B) and one free primer in solution (primer F). Primer B first hybridizes to the original target sequence and is extended, copying the target sequence. The non-attached strand is melted and washed away and new reagent components are added, including a DNA polymerase with strand-displacing properties (such as Bst DNA polymerase), dNTSs, and primer F. A continuous amplification reaction is then used to synthesize a new strand and displace the previous synthesized complement.

The continuous exponential amplification reaction produces a displaced strand, which contains complementary sequences to the capture array oligonucleotide and thus, in turn, is captured and used as a template for further amplification. This process of strand displacement requires that the primer is able to continuously initiate polymerization. There are several described strategies in the art, such as ICAN™ technology (Takara BioEurope, Gennevilliers, France) and SPIA technology (NuGEN, San Carlos, Calif.; U.S. Pat. No. 6,251,639, herein incorporated by reference in its entirety). The property of RNase H that degrades RNA in an RNA/DNA duplex is utilized to remove the primer once extension has been initiated allowing another primer to hybridize and initiate polymerization and strand displacement. In a preferred embodiment, a primer F site is designed in the adapter to be A/T rich such that double-stranded DNA has the ability to frequently denature and allow binding of the F primer at the temperature optimal for the selected DNA polymerase. Approximately 100 to 1000 copies in the ampliot are generated through a continuous exponential amplification without the need for thermocycling.

Yet a further embodiment of the invention incorporates the T7 promoter into the adapter and synthesizes RNA as an intermediate (FIG. 4). Double-stranded DNA is first generated on the slide surface using a nick translating or strand-displacing polymerase. The newly formed strand acts as the template for T7 polymerase and also forms the necessary double-stranded promoter by extension from primer B. Transcription from the promoter produces RNA strands that can hybridize to nearby surface-bound primer, which in turn can be reverse transcribed with reverse transcriptase. This linear amplification process can produce 100-1000 target copies. The cDNA produced can then be converted to single stranded DNA by degradation of the RNA strand in the RNA/DNA duplex with RNase H or by alkali and heat treatment. To minimize intramolecular hybridization of primer B sequence in the RNA molecule, half of the sequence of primer B can come from the T7 promoter sequence, thus reducing the amount of complementary sequences generated to around ten bases.

Both amplification methods are isothermal assuring limited diffusion of the synthesized strands to only within the ampliot region. The ampliot size is about 2 µm, but it can be up to 10 µm because amplified DNA signal can offset a 25-fold increase in total surface background per CCD pixel. Furthermore, primer B attachment sites are spaced at about 10 nm apart (10,000/µm$^2$) providing immediate capture of the displaced DNA. Buffer turbulence is almost eliminated by the enclosed capillary reaction chamber.

Yet a further embodiment of the invention provides a method for isothermal amplification using strand displacement enzymes based on the formation of single-stranded DNA for primer annealing by an invader oligonucleotide (see FIG. 5). Double stranded DNA can be amplified at a constant temperature using two primers, one invader oligonucleotide or other agent, and strand displacement polymerases, such as Klenow fragment polymerase. The invader oligonucleotide is in equal or higher concentration relative to the corresponding primer(s). The target DNA is initially about 100 to 100 million-fold or less concentrated than the primers.

The method of isothermal amplification using an invader oligonucleotide comprises the steps of:

1) Binding of the invader (that can be prepared in part from LNA or PNA or other modifications that provide stronger binding to DNA) to one of the 5'-end sequences of the target DNA by an invasion process. The invader can have a single-stranded or double-stranded overhang (Ds). Invasion can be helped by low duplex stability of $(TA)_x$ or similar sequences that can be added to the corresponding end of the target DNA via an adapter.

2) Hybridizing of primer 1 to the available single stranded DNA site and initiation of primer extension and displacement of one DNA strand by the polymerase. The invader is partially complementary to primer 1. To avoid complete blocking of the primer, the size and binding efficiency of the complementary portion are designed to provide a bound/unbound equilibrium of about 9:1 at the temperature and concentrations used. Approximately 10% of the free primer 1 is in excess over the target DNA.

3) Hybridizing of primer 2 to the opposite end of the single stranded DNA and creation of a new double stranded DNA by the polymerase.

4) Repeating steps 1-3 due to continuous initiation of steps 1-3 by the initial and new dsDNA molecules.

E. Probes and Pools Design

One or more detectable color can be used; however multiple colors would reduce the number of ligation cycles and improve the efficiency of the system. The current state of the art suggests that four colors can be used simultaneously. The preferred embodiment of the invention utilizes FRET-based systems, time resolved systems and time-resolved FRET signaling systems (Didenko, 2001, supra). Custom chemistries, such as quantum dot enhanced triple FRET systems, as well as dendramer technologies are also contemplated.

Two sets of universal probes for FRET-based detection are used in the preferred embodiment. Using the probe design previously described in co-owned U.S. patent application Ser. Nos. 09/479,608 and 10/608,298 (herein incorporated by reference in their entirety) all 4096 possible hexamers with 1024 or less individual synthesis are produced. Probes are subjected to the matriculation and QC (quality control) processing protocols (Callida Genomics, Inc., Sunnyvale, Calif.) prior to use in experiments. Probes are designed to have minimal efficiency difference and actual behavior of each probe with full-match and mismatch targets are determined by the QC assays and used by an advanced base-calling system (Callida Genomics, Inc.).

6.6 Core Technologies

The method of the present invention relies on three core technologies: 1) universal probes, which allow complete sequencing by hybridization of DNA from any organism and detection of any possible sequence alteration. These probes are designed using statistical principles without referring to a known gene sequence (see co-owned, co-pending U.S. patent application Ser. No. 10/608,293, herein incorporated by reference in its entirety); 2) combinatorial ligation, in which two small universal sets of short probes are combined to produce tens of thousands of long probe sequences with superior specificity provided by "enzymatic proofreading" by DNA ligase (see U.S. patent application Ser. No. 10/608,293); 3) informative probe pools (IPPs), mixtures of hundreds of identically tagged probes of different sequences that simplify the hybridization process without negative impact on sequence determination (see U.S. patent application Ser. No. 09/479,608, herein incorporated by reference in its entirety).

The method of the present invention uses millions of single molecule DNA fragments, randomly arrayed on an optically clear surface, as templates for hybridization/ligation of fluorescently tagged probe pairs from IPPs. A sensitive mega pixel CCD camera with advanced optics is used to simultaneously detect millions of these individual hybridization/ligation events on the entire array (FIG. 6). DNA fragments (25 to 1500 bp in length) are arrayed at a density of about 1 molecule per CCD pixel (1 to 10 molecules per square micron of substrate). Each CCD pixel defines a virtual reaction cell of about 0.3 to 1 μm containing one (or a few) DNA fragments and hundreds of labeled probe molecules. The ability of SBH to analyze mixtures of samples and assemble sequences of each included fragment is of great benefit for random arrays. DNA density can be adjusted to have 1-3 fragments that can be efficiently analyzed in more than 90% of all pixels. The volume of each reaction is about 1-10 femtoliters. A 3×3 mm array has the capacity to hold 100 million fragments or approximately 100 billion DNA bases (the equivalent of 30 human genomes).

6.7 Combinatorial SBH

As described above, standard SBH has significant advantages over competing gel-based sequencing technologies, including improvements in sample read length. Ultimately, however, standard SBH processes are limited by the need to use exponentially larger probe sets to sequence longer and longer DNA targets.

Combinatorial SBH overcomes many of the limitations of standard SBH techniques. In combinatorial SBH (U.S. Pat. No. 6,401,267 to Drmanac, herein incorporated by reference in its entirety), two complete, universal sets of short probes are exposed to target DNA in the presence of DNA ligase. Typically, one probe set is attached to a solid support such as a glass slide, while the other set, labeled with a fluorophore, is free in solution (FIGS. 6 and 7). When attached and labeled probes hybridize the target at precisely adjacent positions, they are ligated generating a long, labeled probe that is covalently lined to the surface. After washing to remove the target and unattached probes, fluorescent signals at each array position are scored by a standard array reader. A positive signal at a given position indicates the presence of a sequence within the target that complements the two probes that were combined to generate the signal. Combinatorial SBH has enormous read length, cost and material advantages over standard SBH methods. For example, in standard SBH a full set of over a million 10-mer probes is required to accurately sequence (for purposes of mutation discovery) a DNA target of length 10-100 kb. In contrast, with combinatorial SBH, the same set of 10-mers is generated by combining two small sets of 1024 5-mers. By greatly reducing experimental complexity, costs and material requirements, combinatorial SBH allows dramatic improvements in DNA read length and sequencing efficiency.

6.8 Informative Probe Pools

The efficiencies of combinatorial SBH are further amplified by the use of informative probe pools (IPPs). IPPs are statistically selected sets of probes that are pooled during the hybridization process to minimize the number of combinations that must be tested. A set of IPPs, containing from 4 to 64 different pools, is designed to unambiguously determine any given target sequence. Each pool set comprises a universal set of probes. Pools typically range in size from 16 to 256 probes. When a positive signal results from one or more of these probes, all probes in the pool receive a positive score. The scores from any independent IPP pairings are used to generate a combined probability score for each base position. Accurate sequence data is virtually certain because scores for ten or more overlapping probes, each in different pools, are combined to generate the score for each base position. A false positive score for one probe is easily offset by the correct scores of many others from different pools. In addition, sequencing complementary DNA strands independently minimizes the impact of pool-related false positive probes because the real positive probes for each complementary strand tend to fall, by chance, in different pools. IPPs of longer probes are actually more informative and provide more accurate data than individually scored shorter probes. For example, 16,000 pools of 64 10-mers provide 100-fold fewer false positives than 16,000 individual 7-mers for a 2 kb DNA fragment.

Sets of IPPs will be used to acquire sequence information from arrayed DNA targets. IPPs are carefully selected pools of oligonucleotides of a given length, with each pool typically containing 16 to 128 individual probes. All possible oligos of that length are represented at least once in each set of IPPs. One set of IPPs is labeled with donor fluorophores, the other set is labeled with acceptor fluorophores. These act together to generate FRET signals when ligation between probes from donor and acceptor sets occurs. Such ligation events occur only when the two probes hybridize simultaneously to adjacent complementary sites on a target, thus identifying an 8-10 base long complementary sequence within it. The length of DNA that can be analyzed per pixel is a function of probe length, pool size, and number of pairs of probe pools tested, and typically ranges from 20 to 1500 bp. By increasing the number of pools and/or probes, several kilobases of target DNA can be sequenced. Partial sequencing and/or signature analysis of 1-10 kb of DNA fragments can be accomplished using small subsets of IPPs or even individual probe pairs. IPP pairs may be tested in consecutive hybridization cycles or simultaneously, if multiplex fluorescent labels are used. The fixed position of the CCD camera relative to the array ensures accurate tracking of consecutive hybridizations to individual target molecules.

IPPs are designed to promote strong FRET signals and sequence-specific ligation. Typical probe design includes 5'-$F_x$—$N_{1-4}$—$B_{4-5}$—OH-3' for the first set of IPPs and 5'-P—$B_{4-5}$—$N_{1-4}$—$F_y$-3' for the second set, wherein $F_x$ and $F_y$ are donor and acceptor fluorophores, $B_n$ are specific (informatic) bases, and $N_n$ are degenerate (randomly mixed) bases. The presence of degenerate bases increases the effective probe length without increasing experimental complexity. Each probe set requires synthesizing 256 to 1024 probes and then mixing them to create pools of 16 or more probes per pool, for a total of 8 to 64 IPPs per set. Individual probes may be present in one or more pools as needed to maximize experimental sensitivity, flexibility, and redundancy. Pools from the donor set are hybridized to the array sequentially with pools from the acceptor set in the presence of DNA ligase. Once each pool from the donor set has been paired with the acceptor pool, all possible combinations of 8-10 base informatic sequences have been scored, thus identifying the complementary sequences within the target molecules at each pixel. The power of the technique is that two small sets of synthetic oligonucleotide probes are used combinatorially to create and score potentially millions of longer sequences strings.

The precise biochemistry of the process relies on sequence-specific hybridization and enzymatic ligation of two short oligonucleotides using individual DNA target molecules as templates. Although only a single target molecule is interrogated per pixel at any moment, hundreds of probe molecules of the same sequence will be available to each target for fast consecutive interrogations to provide statistical significance of the measurements. The enzymatic efficiency of the ligation process combined with the optimized reaction conditions provides fast multiple interrogation of the same single target molecule. Under relatively high probe concentrations and high reaction temperatures, individual probes hybridize quickly (within 2 seconds) but dissociate even more rapidly (about 0.5 seconds) unless they are ligated. Alternatively, ligated probes remain hybridized to the target for approximately 4 seconds at optimized temperatures, continuously generating FRET signals that are detected by the CCD camera. By monitoring each pixel for 60 seconds at 1-10 image frames per second, on average 10 consecutive ligation events will occur at the matching target sequences, generating a light signal at that position for about 40 of the 60 seconds. In the case of mismatched targets, ligation efficiency is about 30 fold lower, thus rarely generating ligation events and producing little or no signal during the 60 second reaction time.

The main detection challenge is minimization of background signal, which may result from the required excess of labeled probe molecules. Besides focusing CCD pixels on the smallest possible substrate area, our primary solution to this problem relies on a synergistic combination of surface proximity and the FRET technique (FIG. 7). Long-lasting excitation of the reporting label on one probe will occur only when a pair of probes is aligned on the same target molecule at close proximity to the illuminated surface (for example within a 100 nm wide evanescent field generated by total internal reflection). Thus, background signal will not be generated from excess non-hybridized probes in solution, since either the donor will be too far from the surface to be illuminated, or the acceptor will be too far from the donor to cause energy transfer. In addition, probe molecules can be tagged with multiple dye molecules (attached by branched dendrimers) to increase probe signal over general system background.

After all IPPs are tested, sequence assembly of individual molecules will be performed using SBH algorithms and software (co-owned, co-pending U.S. patent application Ser. No. 09/874,772; Drmanac et al., *Science* 260:1649-1652 (1993); Drmanac et al., *Electrophoresis* 13:566-573 (1992); Drmanac et al., *J. Biomol. Struct. Dyn.* 8:1085-1102 (1991); Drmanac et al., *Genomics* 4:114-128 (1989); U.S. Pat. Nos. 5,202,231 and 5,525,464 to Drmanac et al., all of which are herein incorporated by reference in their entirety). These advanced statistical procedures define the sequence that matches the ligation data with the highest likelihood. The light intensities measured by the CCD camera are treated as probabilities that full-match sequences for the given probe pairs exist at that pixel/target site. Because several positive overlapping probes from different pools independently "read" each base in the correct sequence (FIG. 8), the combined probability of these probes provides accurate base determination even if a few probes fail. Alternatively, multiple independent probes corresponding to incorrect sequences fail to hybridize with the target, giving a low combined probability for that sequence. This occurs even if a few probes corresponding to the incorrect sequence appear positive because they happen to be present in an IPP having a true positive probe matching the real sequence.

6.9 The rSBH Process

The core of the rSBH process of the invention involves the creation and analysis of high-density random arrays containing millions of genomic DNA fragments. Such random arrays eliminate the costly, time-consuming steps of arraying probes on the substrate surface and the need for individual preparation of thousands of sequencing templates. Instead, they provide a fast and cost-effective way to analyze complex DNA mixtures containing 10 Mb to 10 Gb in a single assay.

The rSBH process of the invention combines the advantages of: 1) combinatorial probe ligation of two IPPs in solution to generate sequence-specific FRET signals; 2) the accuracy, long read length, and ability of the combinatorial method to analyze DNA mixtures in one assay; 3) TIRM, a highly sensitive low background fluorescence detection process; and 4) a commercial mega-pixel CCD camera with single photon sensitivity. The method of the invention provides the ability to detect ligation events on single target molecules because long lasting signals are generated only when two ligated probes hybridize to the attached target, bringing donor and acceptor fluorophores to within 6-8 nm of each other and within the 500 nm wide evanescent field generated at the array surface.

The method of the invention typically uses thousands to millions of single molecule DNA fragments, randomly arrayed on an optically clear surface, which serve as templates for hybridization/ligation of fluorescently tagged probe pairs from IPPs (FIG. 6). Pairs of probe pools labeled with donor and acceptor fluorophores are mixed with DNA ligase and presented to the random array. When probes hybridize to adjacent sites on a target fragment, they are ligated together generating a FRET signal. A sensitive mega pixel CCD camera with advanced optics is used to simultaneously detect millions of these individual hybridization/ligation events on an entire array. Each matching sequence is likely to generate several independent hybridization/ligation events, since ligated probe pairs eventually diffuse away from the target and are replaced by newly hybridizing donor and acceptor probes. Non-ligated pairs that hybridize near one another may momentarily generate FRET signal, but do not remain bound to the target long enough to generate significant signal.

Once signals from the first pool are detected, the probes are removed and successive ligation cycles are used to test different probe combinations. The fixed position of the CCD camera relative to the array ensures accurate tracking of consecutive testing of 256 pairs of IPPs (16×16 IPPs) and takes 2-8 hours. The entire sequence of each DNA fragment is compiled based on fluorescent signals generated by hundreds of independent hybridization/ligation events.

DNA fragments (50-1500 bp in length) are arrayed at a density of about 1 molecule per square micron of substrate. Each CCD pixel defines a virtual reaction cell of about 1×1 to 3×3 microns containing one (or a few) DNA fragments and hundreds of labeled probe molecules. The method of the present invention effectively uses the ability of SBH to analyze mixtures of samples and assemble sequences for each fragment in the mix. The volume of each reaction is about 1-10 femtoliters. A 3×3 mm array has the capacity to hold 1-10 million fragments, or approximately 1-10 billion DNA bases, the upper limit being the equivalent of three human genomes.

The length of DNA fragments that can be analyzed per pixel is a function of probe length, pool size, and number of pairs of probe pools tested, and typically ranges from 50 to 1500 bp. By increasing the number of pools and/or probes, several kilobase DNA targets can be sequenced. Partial sequencing and/or signature analysis of 1-10 kb DNA fragments can be accomplished using small subsets of IPPs, or even individual probe pairs.

The rSBH method of the invention preserves all the advantages of combinatorial SBH including the high specificity of the ligation process. At the same time, it adds several important benefits that result from the attachment of DNA fragments instead of probes. DNA attachment creates the possibility of using random DNA arrays with much greater capacity than regular probe arrays and allows FRET detection by ligation of two labeled probes in solution. In addition, having both probe modules in solution allows expansion of the IPP strategy to both probe sets, which is not possible in conventional combinatorial SBH.

6.10 Process Steps rSBH whole-sample analysis has the following processing steps that can be integrated into a single microfluidics chip (FIG. 9):

1) A simple sample treatment or DNA isolation (if necessary), including an effective way to collect pathogen DNA on a pathogen cocktail column;
2) Random DNA fragmentation to produce targets of proper length;
3) Direct end-attachment of DNA to the active substrate surface, for example by ligation to universal anchors;
4) Array washing to remove all unbound DNA and other molecules present in the sample;
5) Introduction of the first IPP pair from two IPP sets at proper probe concentration and T4 ligase or some other (i.e. thermostable) DNA ligase;
6) Incubation for less than 1 min with simultaneous illumination and signal monitoring at 1-10 frames per second;
7) Wash to remove the first IPP pair, followed by introduction of the second IPP pair; and
8) After all IPP pairs are tested, a computer program will generate signature or sequence for each fragment and then compare them with a comprehensive database of signatures or sequences and report the nature of the DNA present in the sample.

6.11 Device Size and Characteristics

The device used with the method of the invention is based on that described in co-owned, co-pending U.S. patent application Ser. No. 10/738,108, herein incorporated by reference in its entirety. The apparatus of the present invention consists of three major components: 1) the handling sub-system for handling (mixing, introducing, removing) IPPs, it is contemplated that this module can be expanded to incorporate "on the chip" sample preparation, 2) the reaction chamber—a flow-through chamber with temperature control that harbors any substrate, and 3) the illumination/detection sub-system (FIG. 10). These sub-systems work together to provide single fluorophore detection sensitivity.

The apparatus of the present invention operates a plug-in reaction chamber with a slot for array substrate and ports for connecting the probe module, and potentially array preparation module, if DNA attachment and/or in situ amplification is done within the chamber.

The cartridge comprises up to 64 individual reservoirs for up to 32 FRET donor pools and up to 32 FRET acceptor pools (FIG. 11). The cartridge comprises a mixing chamber connected to each of the pool reservoirs by means of a single microfluidic channel and an integral vacuum/pressure actuated micro-valve.

6.11.1 The Reaction Chamber

The substrate, once attached to the reaction chamber, forms the bottom section of a hybridization chamber. This chamber controls the hybridization temperature, provides ports for the addition of probe pools to the chamber, removal of the probe pools from the evanescent field, redistribution of the probe pools throughout the chamber, and substrate washing. A labeled probe pool solution is introduced into the chamber and is given time to hybridize with the target DNA (a few seconds). Probes not involved in a hybridization event are pulled out of the evanescent field by creating a voltage potential in the hybridization solution. A high sensitivity CCD camera capable of single photon detection is used to detect FRET hybridization/ligation events (Ha, *Methods* 25:78-86 (2001), herein incorporated by reference in its entirety), by monitoring the substrate through a window at the top of the reaction chamber. Images of the substrate are taken at regular intervals for about 30 seconds. The chamber is then flushed to remove all probes and the next probe pool is introduced. This process is repeated 256-512 times until all probe pools have been assayed.

6.11.2 The Illumination Sub-System

The illumination sub-system is based on the TIRM background reduction model. TIRM creates a 100-500 nm thick evanescent field at the interface of two optically different materials (Tokunga et al., *Biochem. Biophys. Res. Commun.* 235:47-53 (1997), herein incorporated by reference in its entirety). The apparatus of the present invention uses an illumination method that eliminates any effect that the Gaussian distribution of the beam would have on the assay. The laser and all other components in this sub-system of the device of the present invention are mounted to an optical table. A 1 cm scan line is created by moving the mirrors mounted on galvanometers 1 and 2 FIG. 10). The scan line is then directed into the substrate through prism 1 by galvanometer 3. Galvanometer 3 is adjusted so that the scan line intersects the glass/water boundary at its critical angle. The beam undergoes total internal reflection creating an evanescent field on the substrate. The evanescent field is an extension of the beam energy that reaches beyond the glass/water interface by a few hundred nanometers (generally between 100-500 nm). The evanescent field of the invention can be used to excite fluorophores close to the glass/water boundary and virtually eliminates background from the excitation source.

6.11.3 The Detector Sub-System

The device of the present invention uses a high sensitivity CCD camera (such as DV887 with 512×512 pixels from Andor Technology (Hartford, Conn.)) capable of photon counting which is suspended above the hybridization chamber. The camera monitors the substrate through the window of the reaction chamber. The lens on the camera provides enough magnification so that each pixel receives the light from 3 square microns of the substrate. In another embodiment, the camera can be water-cooled for low-noise applications.

The highly sensitive electron multiplying CCD (EMCCD) detector makes high-speed single fluorophore detection possible. Assuming a 1 Watt excitation laser at 532 nm (for Cy3/Cy5 FRET), the number of photons emitted from the laser every second can be calculated and the number of photons which will reach the detector every second can be estimated. Using the equation $e=hc/\lambda$, wherein $\lambda$ represents wavelength, a photon with a 532 nm wavelength has an energy of $3.73e-19$ Joules. Given the laser output is one Watt, or one Joule/second, it is expected that $2.68e18$ photons per second are emitted from the laser. Expanding this amount of energy across the 1 $cm^2$ substrate area, it is expected that each square nm will receive about $1e-15$ Joules of energy, or about 26,800 photons. Assuming a quantum yield of 0.5 for the fluorophore, an output of about 13,400 photos per second is expected. Using a high quality lens, about 25% of the total output should be collected or a total of 3350 photons, which are captured by the CCD. Andor's DV887 CCD has a quantum efficiency of about 0.45 at 670-700 nm where Cy5 emits. This yields approximately 1500 photons per second that each pixel registers. At 10 frames per second, each frame registers 150 counts. The dark current of the camera at $-75°$ C. is about 0.001 electrons/pixel/sec, on average 1 false positive count every 1000 pixels once a second. Even if a 1 false positive count per pixel per second is assumed, at 0.1 per pixel per frame, a 1500:1 signal to noise ratio is obtained. In combination with the TIRM illumination technique, the detector background is virtually zero.

6.11.4 Miniaturization of the Device

In another embodiment, the method of the present invention can be performed in a miniature device. A simple physical device, requiring only a few off-the-shelf components, can perform the entire process. The illumination and detection components form the core of the system. This core system consists of only a CCD camera, a laser or other light source, none to three scanning galvanometers, quartz or equivalent supports for the substrate, and a reaction chamber. It is possible to place all of these components in a one cubic foot device. A miniature fluid-handling robot or micro-fluidics lab-on-a-chip device (FIG. 9) will perform the assay by accessing pairs of IPPs from two libraries of 8 to 64 IPPs and can occupy about 0.5 $ft^3$. High-density multi-well plates or lab-on-a-chips with 64 reservoirs will allow for ultra-compact storage of the library. A single board computer or laptop can run the device and perform the analysis. Such a system is easily transportable and can fit into almost any vehicle for field surveying of the environment or responding to emergency crew or biohazard workers. It is also possible for the device to fit in a medical pack and run on battery power to perform rapid, accurate screening in the field under almost any circumstance.

The components of the system include: 1) miniature personal computer (1 ft×1 ft×6 in), 2) robotic or lab-on-a-chip fluid handling system (1 ft×1 ft×2 in), 3) laser (6 in cube), 4) scanning galvanometers with heat sink (3 in cube), 5) slide/hybridization chamber assembly (3 in×1 in×2 in), 6) CCD camera (4 in×4 in×7 in), and 7) fluid reservoirs (approximately 10-1000 ml capacity).

Another embodiment of the device of the invention integrates a modular micro-fluidics based substrate upon which all assays are conducted for pathogen detection (FIG. 11). The consumable substrate is in the form of an integrated "reaction cartridge." The substrate component of the cartridge must accept three different kinds of integrated disposable modules including: probe pool module, sample integration module, and reaction substrate module. All machine functions act on this cartridge to produce the assay result. This substrate requires integrated fluidics such as quick connects which the reaction cartridge and related modules will provide.

Microfluidics is introduced to the substrate in order to handle informational probe pools on the detection surface of the substrate. A modular approach is used in which the initial probe-handling module is developed independent of the substrate and the final design can be added to the standard substrate cartridge using a "plug and play" approach. The cartridge contains up to 64 individual reservoirs for 32 FRET donor pools and up to 32 FRET acceptor pools (see FIG. 11). A larger number of IPPs can be stored on one or a set of cartridges, for example 2×64, or 2×128, or 2×256 or 2×512 or 2×1024 IPPs. The cartridge has a mixing chamber connected to the main channel by its own microfluidic channel and an integral vacuum/pressure actuated micro-valve. When the valve is opened, a vacuum is applied to move a pool into the mixing chamber. The valve is then closed, and the process is repeated to add the second pool. The mixing chamber is in line with the wash pump, which is used to agitate the pools and push them into the reaction chamber.

6.12 Software Components and Algorithms

Row data represents about 3-30 intensity values at different time/temperature points for each pair of pools (i.e. IPPs) in each pixel. Each value is obtained by statistical processing 10-100 CCD measurements (preferably 5-10 per second). Each fragment has 512 sets of 3-30 intensity values. An array with one million fragments comprises about 10 billion intensity values. Signal normalization can be performed on groups of hundreds of pixels. All data points for a given pair of IPPs will be discarded if the set does not meet expected behavior. Each pixel (most of which will have proper DNA) with no useful data (i.e. not enough positive or negative data points) will be discarded. The distribution of intensity values in other pixels will be determined and used to adjust base calling parameters.

All individual short fragments can be mapped using a score signature to a corresponding reference sequence and analyzed using comparative sequencing processes or is sequence assembled using de novo SBH functions. Each approximately 250 base fragment is assembled from about one million possible 10-mers starting from the primer sequences. The assembly process proceeds through evaluation of combined 10-mer scores calculated from overlapping 10-mers for millions of local candidate sequence variants.

A group of fragments from one array location that has significant overlapping sequences with groups of fragments from other array locations represents a long continuous genomic fragment. These groups can also be recognized by alignment of short fragment sequences to a reference sequence, or as an island of DNA containing pixels surrounded by empty pixels. Assigning short fragments to groups, especially in partially structured arrays, is an intriguing algorithmic problem.

Short fragments within a group have originated from a fragmented single DNA molecule and do not overlap. But short sequences do overlap between corresponding groups, representing long, overlapping DNA fragments and allow assembly of long fragments by the process identical to sequence assembly of cosmid or BAC clones in the shotgun sequencing process. Because long genomic fragments in the rSBH process vary from 5-100 kb and represent 5-50 genome equivalents, the mapping information is provided at all relevant levels to guide accurate contig assembly. The process can tolerate omissions and errors in assignment of short fragments to long fragments and about 30-50% randomly missing fragments in individual groups.

The rSBH method of the invention provides detection of rare organisms or quantification of numbers of cells or gene expression for each microbe. When the dominant species has 1× genome coverage, then the species that occurs at the 0.1% level are represented by about 10 genomic fragments. DNA normalization can further improve detection sensitivity to 1 cell in more than 10,000 cells. DNA quantification is achieved by counting the number of occurrences of DNA fragments representing one gene or one organism. The absence of the cloning step implies that rSBH should provide a more quantitative estimate of the incidence of each DNA sequence type than conventional sequencing. For quantification studies, direct fragmentation of sample to 250 bp fragments and formation of standard (non-structured) random arrays is sufficient. Partial normalization can be used to minimize but still keep occurrence difference and standardization curves can be used to calculate original frequencies. An array of one million fragments is sufficient for quantification of hundreds of genospecies and their gene expression.

6.12.1 rSBH Software

The present invention provides software that supports rSBH whole-genome (complex DNA sample) sequencing. The software can scale up to analysis of the entire human genome (~3 Gbp) or mixtures of genomes up to 10 Gbp. Parallel computing on several CPUs is contemplated.

The rSBH instrument can generate a set of tiff images at the rate of up to 10/sec or faster. Each image represents a hybridization of the target to pairs of pooled labeled probes. Multiple images may be produced for each hybridization to provide signal averaging. The target is fragmented in multiple pieces approximately 100 to 500 bases long. The fragments are attached to the surface of a glass substrate in a random distribution. After hybridization and wash of the non-hybridized probes, the surface is imaged with a CCD camera. Ultimately, each pixel of the image may contain one fragment, although some pixels may be empty while others may have two or more fragments. The instrument can potentially image 1-10 million, or even more fragments.

The total instrument run time is determined by the hybridization/wash/image cycle (~1 min.) multiplied by the number of pool sets used. With 1024 pool sets (producing 1024 images), the run will last about 17 hours; two colors reduce this by one half. The image analysis software will process the images in near real time and send the data to the base-calling analysis software.

A. Parallel Processing

The rSBH analysis is ideally suited to parallel processing. Because each "spot" hybridizes to a different fragment, the base-calling analysis can be run in parallel on each spot with no need for communication between the analyses. The only communication in the entire analysis is between the control module (GUI) and the analysis programs. Very minor steps need to be taken to avoid race conditions. In practice the number of CPU's limits the number of parallel processes. For one million fragments a computer with 100 processors will split the job into 100 parallel base-calling programs which each analyze 10,000 or more fragments, in series.

A set of 200 fragments can be run on one processor, however it can also be run on several CPU's. An optimized base-calling program can finish in ~100 milliseconds if there are no mutations or mutation tests (update function). This time includes data loading and normalizations. Reference lookup time can add ~100 milliseconds for the longest reference (see below). Reference lookup time scales with length and is negligible for the short lengths. Analyzing multiple mutations can extent the run time up to about one minute per multiple mutation site. If the average analysis time is one second per fragment, one million fragments can be analyzed in 10,000 seconds using 100 CPU's. Similarly, 200 fragments can be analyzed in 200 seconds using one CPU or 20 seconds using 10 CPU's. Optimizing the programs for speed requires a significant amount of RAM per CPU. As described below, the software is not limited by memory if each CPU has ~2 GB to 8 GB, depending on the number of CPU's and number of fragments. Currently it is possible to purchase 32 GB+ of RAM per system.

B. Data Flow

The GUI and image analysis program run on one CPU, while the base calling analysis programs run on several (N) CPU's. On startup, the image analysis program is supplied with the number N and monitors the directory that the CCD camera writes tiff images into. For each tiff file, it derives a score for each fragment and group the scores into N files, one for each analysis CPU. For example, if there are 200 fragments and 10 CPU's, the image analysis program writes the first 20 fragment scores into a file for the first base-calling analysis CPU, the second 20 fragment scores into a second file for the second base-calling analysis CPU, and so on. It is also contemplated that other communication modes can be used, for example sockets or MPI. Therefore, the file I/O can be localized to one module so that it can easily be swapped out later.

Over time there a multitude of image analysis files is created for the continually growing number of tiff files. The invention provides for a separate image analysis directory for each base-calling analysis CPU. The bases-calling analysis CPU's each monitor their respective image analysis directories and load the data as it becomes available. The amount of RAM/CPU necessary to store all the image data is [2 bytes× no. fragments×no. images÷N]. This is ~2 GB/CPU for 1 million fragments, 1024 images and 1 CPU, or 200 KB/CPU for 10 CPU's.

The other significant (in terms of RAM) data input to the base-calling analysis program is the reference (length L). For speed optimization, the reference is converted to a vector of 10-mer (and 11-mer, 12-mer) positions providing for a quick lookup for the top scoring probes for each fragment (see below). It is fastest to store the reference position data on every base-calling analysis CPU. The amount of memory required to store the reference position data is 2 bytes×L, or 2 bytes×$4^{12}$, which ever is greater. The maximum RAM is 2 bytes×10 GB=20 GB. The actual reference itself must also be stored, but this can be stored as 1 byte/base or even compressed to 0.25 bytes/base.

Analysis of each fragment generates a called sequence result. These are concatenated into a file that is written to the image analysis directory associated with each CPU. When base calling is complete, the GUI processes the called sequence files. It loads all files, from the different CPU's, and reorders the fragments by position to generate a final complete called sequence. Note that reordering is trivial, as each fragment was located previously during the reference lookup step. The GUI can also provide a visualization tool of the called sequence. In addition, the GUI can display an intensity graph of the final sequence. In this case the base-calling program must also output the intensity files (concatenated as the called sequence data).

The current base calling program outputs a Short Report file based on the reference and spots scores (from the HyChip™ for example). This may not be useful for rSBH since the spots for each fragment are distributed among many hybridization slides. Instead, a new "Short Report" can be generated for each hybridization that is more abstract than the HyChip Short Report. Specifically, the new report can list the number (N) of full matches on each slide and the median of the highest N scores. It can also give the median of any control spots such as markers or empties if any exist. The advantage of the new report is that is can be viewed in real time for each image on a constantly updated GUI table. This will tell the user early on (and throughout the run) if the rSBH system is generating useful data, instead of waiting a day to see the final results. An advanced use of the new report allows user feedback to the rSBH instrument. For example, pausing/stopping the run from the GUI or repeating a pool set if any one failed. The GUI can also display instrument parameters in real time during a run, such as hybridization and wash temperatures. Ultimately, the product can integrate the instrument into the command and control module of the user GUI.

C. Base Calling

Since the pooled probes are the same for each fragment, the rSBH base-calling program can read in the pooled probes only once for all fragments. The base-calling program requires a reference sequence input. For rSBH, the reference is derived from an analysis of the clustering of the top few hundred scores. A simple binning algorithm of the positions of the top scores is most efficient, since it requires a single pass through the binned positions to find the maximum bin counts. The window of maximum bin counts locates the position of the fragment in the reference. With 250 bp fragments and 1024 measurements, ¼ of the fragment scores are positive (i.e. full match hybridization score). Then, due to the complexity of the pooled probes, ¼ of the 10-mers represent positive scores. Furthermore, for a reference longer than $4^{10}$, the probes are repeated, so that ¼ of all 10-mers in the reference are positive. The same applies for 11-mers and 12-mers; ¼ of all reference probes are positive. For a processor able to bin one probe in 1 nsec, it would take [L÷4÷$10^9$] seconds to find the reference for a fragment. For the extreme L=10,000,000,000, this is 2.5 seconds/fragment using one CPU. For 1 million fragments and 100 CPU's the total time to find the references is ~25,000 seconds (6-8 hours).

An alternative to binning the top L scores is to perform a de novo type of sequence assembly on each fragment to reduce the number of probes to much less than 250 used in the example above. This will speed the fragment lookup process if the de novo algorithm is fast (e.g. less than 1 msec). A fast de novo algorithm can involve finding a few sets of 10 or more of the top 250 scores that have overlapping probes and can reduce required time an order of magnitude or more.

D. Base Calling Algorithm

1. Read probe pool files
2. Read reference (length RL) and store into Reference object.
2a. Generate reference positions data structure.
3. Read intensity files (in real time as they are generated from image analyses).
3a. Store values into Scores data structure.
4. Accumulate about top L scores for each fragment (of median length L).
5. Analysis loop for each fragment:
5a. Create a list of positions in the reference for the top L scores.
5b. Create a vector whose length is [RL÷(m×L)], to bin the top score positions into. This gives a bin length of m×L, where m should be ~1.5 to provide a margin on either side of the fragment.
5c. Bin the positions for the top L scores into the binning vector.
5d. Find the region of highest total bin count. This gives the fragment reference to within (m−1)×L base positions.
5e. Perform base calling using fragment reference.
5f. Concatenate the called sequence onto a file: called Sequence (include the position information)
6. End of analysis loop for each fragment.

6.13 Additional Embodiments

The method of the present invention allows for multiple mechanisms by which probes and IPPs are designed. In one embodiment, probes and IPPs are designed by varying the number of probes per pool, more specifically, in the range of 4 to 4096 probes per pool. In a second embodiment, probes and IPPs are designed by varying the number of pools per set, more specifically in the range of 4 to 1024 pools per set. Probes may have 2 to 8 informative bases providing a total of 4-16 bases. In yet another embodiment, probes are prepared as pools with degenerate synthesis at some positions. A further embodiment comprises having two assemblies of two sets of IPPs wherein different probes are mixed within one pool.

A small set of 20 to a few hundred probes can provide a unique hybridization signature of individual nucleic acid fragments. Hybridization patterns are matched with sequences to identify pathogens or any other nucleic acid, for example for counting mRNA molecules. One embodiment of the method of the invention uses signatures to recognize identical molecules on different random arrays. This allows, after hybridizing the same set of probes on different arrays to produce signatures, hybridization of different subsets of test probes on different arrays prepared from the same sample followed by combination of data per individual molecules.

Another embodiment of the method of the invention performs single molecule DNA analysis without combinatorial ligation, using only a single set of IPPs or individual probes.

In this embodiment, FRET signals are detected by labeling the target with a donor fluorophore and the probes with an acceptor fluorophore, or labeling the target with an acceptor fluorophore and the probes with a donor fluorophore. Probes in the form of 5'-$N_x$—$B_{4-16}$—$N_y$-3' may be synthesized individually or as pools containing degenerate (mixed) bases at particular positions. In another embodiment, probe/probe pool hybridization are combined with polymerase-based extension of the hybridized probe by incorporation of one or more labeled nucleotides, wherein the nucleotides are typically differentially labeled.

Another embodiment of the method of the present invention utilizes probe removal to achieve multiple tests of a target molecule with the same probe sequence, probe molecules can be repeatedly removed from and toward the support surface using electric field, magnetic field, or solution flow. The cycles occur from every 1-10 seconds up to 20-30 seconds. Fluorescent signals are recorded for each phase of the cycle or alternatively, only after probe removal is initiated, or only after probe removal is completed. The removal is coupled with temperature cycling. In this embodiment, probe removal does not require FRET labeling and instead relies on direct fluorescence from one label. Alternatively, the FRET reaction occurs between a labeled probe and a dye molecule attached to a target molecule.

A further embodiment of the method of the invention involving repeated testing of a probe sequence utilizes repeated loading of the same probe species from the outside container into the reaction chamber. A quick removal of the previous probe load is first followed with a wash buffer that does not remove full-match hybrids (the product of ligation of two probes if ligation is used), but removes free probes. A second wash is used that melts all hybrids before a subsequent probe load is introduced.

In another embodiment, each probe species interaction with a target molecule is measured only once. This process relies on redundant representation of the same DNA segment at different places within the array and/or on the accuracy of a one-time ligation event.

In addition to preparing final fragments before loading a sample on the support to form an array, a two-level cutting procedure is used in another embodiment of the method of the invention. Sample DNA is first randomly cut to form longer fragments (approximately 2-200 kb or more). A mixture of these fragments is loaded on the support that may be patterned by hydrophobic material in the form of a grid comprising cells of approximately 10×10 $\mu m^2$ in size. Concentration of the sample is adjusted such that predominantly one or a few long fragments will be present in each cell. These fragments will be further randomly fragmented in situ to a final fragment length of approximately 20-2000 bases and attached to the support surface. The optimal cell size depends on the total length of the DNA introduced per cell, the preferred length of the final fragments, and the preferred density of the final fragments. This fragmentation method of the invention provides long-range mapping information because all short fragments in one cell belong to one or a few long fragments from long overlapping fragments. This inference simplifies the assembly of long DNA sequences and may provide whole chromosome haplotype structure.

In another embodiment of the present invention, selected target DNA is captured from the complex sample using, for example, a column containing an equalized number of DNA molecules for certain genes or organisms. For example, selected viral or bacterial genomes or parts of genomes can be represented on these columns in the form of attached single-stranded DNA (ssDNA). Sample DNA is melted if double-stranded DNA (dsDNA) and complementary strands are captured by hybridization to immobilized DNA. The excess of complementary DNA or any other unrelated DNA is washed out. The captured DNA is then removed by high temperature or chemical denaturation. This process can be used to remove human and other complex DNA for diagnostics of infectious agents. It also provides a method to reduce the concentration of over-represented agents in order to detect other agents present in a low copy number present on a smaller array. The capture process can be performed in tubes, wells of multi-well plates or in microfluidics chips.

Selection of specific genes or other genomic fragments is achieved by cutting DNA with restriction enzymes with downstream cutting and ligation of matching adaptors (described in co-owned, co-pending U.S. patent application Ser. No. 10/608,293, herein incorporated by reference in its entirety). Fragments that are not captured by adapters will be depredated or otherwise removed. Another embodiment uses oligonucleotides of 6-60 bases, or more preferably, 10-40 bases, or even more preferably, 15-30 bases designed to match a given sequence with one or more mismatches allowing cutting of DNA using mismatch recognition along with cutting enzymes. Two oligonucleotides can be designed for cutting complementary strands with about a 1-20 base shift creating a sticky end for ligation of an adaptor or ligation to a vector arm. Two pairs of such oligonucleotide cutting templates from a genomic fragment can be obtained and captured or end modified for capture with a specific adaptor(s). Cutting templates are synthesized, or alternatively, one or more libraries of short oligonucleotides are designed to provide a universal source of necessary cutting templates for any DNA. Libraries of 256 oligonucleotides represented by the following consensus sequences nnnbbbnn, nnbbbbnn, or cggnnnbbbbnn, nnbbbnn, nnbbbnnncac, wherein n represents a mixture of four bases or a universal base, b represents a specific base, bbbb represents one of 256 possible 4-mer sequences, cgg and cac represent examples of specific sequences shared by all members in the library, can be used to create cutting templates. To create cutting templates, an assembly template of nnnnnnnnnnnnnnnnnn or gccnnnnnnnnnnnnnnnnnnnnnnnnnngtg, may be used to ligate two or three members selected from corresponding oligonucleotide libraries.

In addition to various chemical attachment approaches, DNA fragments prepared by random cutting or by specific cutting may be attached to the surface using adaptors attached to fragments of anchors, adaptors, primers, other specific binders attached to the surface or both. One embodiment uses randomly attached anchors with sticky ends of approximately 1-10 bases in length and ligates ssDNA fragments or dsDNA fragments with matching sticky ends. Sticky ends may be provided by adaptors attached to DNA fragments. This approach provides the possibility to have sections of substrate with anchors having different sticky ends to identify the end sequence of the attached fragment. Another embodiment attaches the primer to a support that is complimentary to an adaptor attached to a DNA fragment. After ssDNA hybridizes to primers, the polymerase is used to extend the primer. The produced dsDNA is melted to remove strand that is not attached to the support of use for DNA amplification as described below. Yet another embodiment coats the surface with specific binders (for example, cyclic peptides) that recognize 3' or 5' ends of DNA fragments and binds them with high affinity.

Analysis of short fragments attached to adaptors on one or both sides may help in reading through palindromes and hairpins because when there is a cut within a palindrome/hairpin, a new adaptor sequence will be attached that is not complementary to the rest of the sequence. Adaptors allow every base of the target DNA to be read with all overlapping probes.

In yet another embodiment, detection accuracy and efficiency is increased by using random arrays of single molecules followed by in situ, localized amplification (Drmanac and Crkvenjakov, 1990, supra, herein incorporated by reference) to generate up to 10, up to 100, up to 1000, up to 10,000 replica molecules attached within the same pixel area. In this case, there is no need for single molecule sensitivity because multiple scores of probes are not necessary, even though FRET and TIRM may still be used. The amplification process comprises the following steps: 1) using a support coated with one primer (about 1000-50,000 primer molecules/$\mu m^2$), 2) using sample DNA fragments modified with a ligated adaptor and second primer in solution. There is a need to minimize mixing and diffusion, for example by using a capillary chamber (a cover slip with only 10-100 µm space from the support) or embedding the target and second primer in a gel. The population of molecules generated by amplification for a single target molecule will form a spot, or "amplicon", that should be less than 10-100 µm in size. Amplification of hybridization or ligation events may also be used to increase the signal.

A preferred embodiment uses continuous isothermal amplification (i.e. different types of strand displacement) because there is no need to denature dsDNA using high temperature, which can cause large-scale diffusion or turbulence, the displaced strand has no other complementary DNA to bind to other than the attached primer, and a high local concentration of DNA can be produced. Another embodiment using isothermal amplification is to design at least one adaptor (for one end of the target DNA) with a core sequence that has a low melting temperature (i.e. using TATATAT . . . sequence having between 3-13 TA repeats) and primers substantially matching to this core sequence. At the optimal temperature for the polymerase capable of strand displacement used in this reaction, the dsDNA at the TATATA . . . site will locally melt allowing hybridization of the primer and initiation of a new cycle of replication. The length (i.e. stability) of the core can be adjusted to accommodate temperatures between 30-80° C. In this Continuous Amplification Reaction (CAR), new strand synthesis can start as soon as the enzyme performing the previous synthesis moves from the priming site, which takes about a few seconds. The process is used to produce high concentrations of ssDNA starting with dsDNA if only one primer is used. For amplification where one primer is attached to the surface, the low temperature melting adaptor should be for the non-attaching end and the corresponding primer will be free in solution. CAR does not require any other enzymes in addition to the polymerase. Adaptors are introduced by ligation with DNA fragments or tail extensions of target specific primers for two or more initial amplification cycles on source dsDNA that may require melting by high temperature.

The nucleic acid analysis processes described above based on probe/probe pool hybridization alone or in combination with base extension or two probe ligation to random arrays of sample DNA fragments is used for various applications including: sequencing of longer DNA (including bacterial artificial chromosomes BACs) or entire viruses, entire bacterial or other complex genomes) or mixtures of DNA; diagnostic sequence analysis of selected genes; whole genome sequencing of newborn babies; agricultural biotech research for precise knowledge of the genetic makeup of new crops and animals; individual cell expression monitoring; cancer diagnostics; sequencing for DNA computing; monitoring the environment; food analysis; and discovery of new bacterial and viral organisms.

The method of the present invention generates sufficient signal from a single labeled probe while reducing the background below the threshold of detection. Special substrate material or coating (such as metallization) and advanced optics are used to reduce high system background that prevents parallel detection of millions of single molecules from a 1 $cm^2$ surface. Alternatively, background that is introduced with the sample or during the DNA attachment process is reduced by special treatment of the sample, including affinity columns, modified DNA attachment chemistry (e.g. ligation), or binding molecules (e.g. cyclic peptides) with exclusive DNA specificity. In some instances, reduction of background produced by non-ligated probe complexes in solution or assemblies on the substrate requires cyclic removal of non-hybridized/ligated probes by electric field pulsing, specially engineered ligase with optimized thermal stability and full match specificity, or triple FRET system with a third dye (e.g. quantum dot) attached to the target molecule.

In another embodiment, the method of the invention requires concentration of DNA molecules on the support by an electric field in order to capture all fragments from a chromosome or genome on a random array surface. Chromosome fragmentation to allow correct assembly may require compartmentalized substrate and in situ fragmentation of initial individual 100 kb to 1 Mb DNA fragments to obtain linked groups of shorter 1-10 kb fragments.

Obtaining fast hybridization/ligation to allow multiple interrogations of the target with one pair of probe pools in less than 60 seconds/cycle may require the use of optimized buffers and/or active probe manipulation, potentially using electromagnetic fields. Fluorescent dyes (or dendrimers) with excitation properties compatible with DNA stability and precise control of illumination (nanosecond laser pulsing) are used to increase the chemical and physical stability of the system (including arrayed target DNA molecules) to tolerate several hours of illumination.

Fast real time image processing and assembly of individual fragments from overlapped probes and entire genome from overlapped DNA fragments may require programmable logic arrays or multiprocessor systems for high speed computation.

The method of the present invention relies on specific molecular recognition of complementary DNA sequences by labeled probes and DNA ligase to generate visible fluorescent signals. By relying on naturally evolved sequence recognition and enzymatic proofreading processes, rSBH eliminates the significant technical challenges of physically distinguishing individual DNA bases that are only 0.3 nm in size and differ by only a few atoms from one another. The method of the present invention also has very simple sample preparation and handling involving random fragmentation of chromosomal or other DNA and formation of small (1-10 mm$^2$), random single-molecule arrays containing approximately one DNA molecule per square micron. The method of the present invention simultaneously collects high speed data on millions of single molecule DNA fragments. Using ten fluorescent colors and a 10 mega pixel CCD camera, a single rSBH device can read 10$^5$ bases per second. The read length of the present invention is adjustable, from about 20-20,000 bases per fragment, and totaling up to 100 billion bases per single experiment on one random array. By initial fragmentation of individual long fragments and attachment of corresponding groups of short fragments to isolated random sub-arrays, the effective read length of the rSBH process may be up to 1 Mb. Maximal sequencing accuracy assured by obtaining 100 independent measurements per base for each single DNA molecule tested (i.e. 10 overlapping probe sequences, each tested on average by 10 consecutive ligation events to the same DNA molecule).

Combinatorial SBH using LPPs provides over 99.9% accurate sequence data on PCR amplified samples several thousand bases in length. This read length is many times longer than that obtained by currently used gel-based methods and provides whole gene sequencing in a single assay. The method of the present invention combines the advantages of parallelism, accuracy and simplicity of hybridization-based DNA analysis with the efficiency of miniaturization and low material costs of single molecule DNA analysis. Application of universal probe sets, combinatorial ligation and informative probe pools allows efficient and accurate analysis of any and all DNA molecules and detection of any sequence changes within them using a single small set of oligonucleotide probe pools. The method of the present invention uses an integrated system to apply well-known biochemistry and informatics on ultra-high density, random single-molecule arrays to achieve a dramatic 1,000 to 10,000 fold higher sequencing throughput than in current gel and SBH sequencing methods. The method of the present invention will allow sequencing of all nucleic acid molecules present in complex biological samples, including mixtures of bacterial, viral, human and environmental DNA without DNA amplification or manipulation of millions of clones. Minimized sample handling and low chemical consumption and a fully integrated process will decrease the cost per base, at least as much as 1,000 fold or more. The method of the present invention is capable of sequencing the entire human genome on a single array within one day.

Random arrays of short DNA fragments are easily prepared at densities 100 fold higher than most standard DNA arrays currently in use. Probe hybridization to such arrays and advanced optics allows the use of mega-pixel CCD cameras for ultra-fast parallel data collection. Each pixel in the array monitors hybridization of a different DNA molecule providing tens of millions of data points at a rate of 1-10 frames per second. Random arrays can contain over 100 billion base pairs on a single 3×3 nun surface with each DNA fragment represented in 10-100 pixel cells. The inherent redundancy provided by the SBH process (in which several independent overlapping probes read each base) helps assure the highest final sequence accuracy.

To achieve the full capacity of the ligation method of the invention, which allows reading of up to 1000 bases per molecule, multiple IPP reagents must be handled simultaneously. The ligation method of the invention eliminates the need to covalently modify every target molecule analyzed. Because SBH probes are not covalently attached to targets, they can be easily removed or photo-bleached between cycles. In addition, the inclusion of a polymerase ensures that a base can be tested only once in any given DNA molecule. The hybridization/ligation process of the present invention allows multiple interrogations with each given probe and multiple interrogation of each base by several overlapping probes, providing a 100 fold increase in the number of measurements per base. In addition, ligase allows larger tag structures to be utilized (i.e. dendrimers with multiple fluorophores or Q-dots) than polymerase, which may further increase detection accuracy.

The method of the present invention can generate universal signature analysis of long DNA molecules using smaller incomplete sets of long universal probes. Single molecules up to 10 kb may be analyzed per pixel. An array of 10 million fragments, each 10,000 bp in length, contains one trillion (10$^{12}$) DNA bases, the equivalent of 300 human genomes. Such an array is analyzed with a single 10 mega pixel CCD camera. Informative signatures are obtained in 10-100 minutes depending on the level of multiplex labeling. An analysis of a 10- or 100- or 1000-fold smaller array is very useful for signature or sequencing or quantification applications.

In one embodiment, a single pathogen cell or virus is represented with 10-10,000 fragments in the array, thereby eliminating the need for DNA amplification. The single molecule signature approach of the instant application provides a comprehensive survey of every region of the pathogen genome, representing a dramatic improvement over multiplex amplification of thousands of DNA amplions analyzed on standard probe arrays. DNA amplification is a non-linear process and is unreliable at a single molecule level. Instead of amplifying a few segments per pathogen, the concentration of unwanted or contaminating DNA is reduced using pathogen affinity columns, and the entire genome of the collected pathogens can be analyzed. A single virus or bacterial cell can be collected from among thousands of human cells and is represented by 1 to 10 kb fragments on 10-1000 pixels, providing accurate identification and precise DNA categorization.

In another embodiment, the method of the present invention is used to detect and defend against biowarfare agents. rSBH identifies structural markers allowing immediate detection of bioagents at a single organism level before pathogenicity and symptoms develop. rSBH provides a comprehensive analysis of any or all of the genes involved in the pathogen's mode of attack, virulence, and antibiotic sensitivities in order to quickly understand the genes involved and how to circumvent any or all of these genes. rSBH can analyze complex biological samples containing mixed pathogens, host, and environmental DNA. In addition, the method of the invention is used to monitor the environment and/or personnel using rapid, low cost comprehensive detections methods and can be made portable.

6.14 Kits

The present invention also provides for IPP kits to load on the cartridge or cartridges with preloaded probes as products, optionally including ligation mix with buffer and enzyme.

The present invention also provides for pathogen/gene-specific sample preparation kits and protocols for pathogens such as *Bacillus anthracis* and *Yersina pestis*, from, for example, blood samples. The present invention provides for integration of sample preparation DNA products into the substrate resulting in the formation of the rSBH array of the invention. A stepwise process is described that yields an array of an individual target per pixel and an optional in situ amplification yielding 10-1000 copies per pixel. The result is a random array of target DNA that is subjected to rSBH for sequence analysis. The modular approach of the invention to the evolving substrate allows early versions of the substrate to have a simple sample application site, whereas final development may have a "plug and play" array preparation module.

DNA samples meeting the minimal purity and quantity specifications will serve as starting material for real sample integration with the rSBH sample arraying technology. Sample integration begins with enzymatic digestion (restriction enzyme or nuclease digest) of the products from the crude sample creating specific (or random) sticky ends providing fragments roughly 250 bp in length. This enzyme cocktail represents one of several components that would be provided in a product kit.

Arraying of the digest involves ligation of the sticky ends to complements arrayed onto the surface. The array surface is modified from its original glass surface as follows: 1) formation of an aminopropylsilane monolayer; 2) activation with a symmetric di-isothiocynate; and 3) using a novel cocktail of aminolated oligonucleotides (including capture probes, primer probes and spacer probes) the activated array surface is modified with a heterogeneous monolayer of probes.

All of the attached probes share a conserved design (>90%), thus preventing the formation of homogeneous islands in which spacer and capture probes are segregated. The ratio of capture probe to all other probes gives rise to an average density equal to 1 complementary ligation site (for sample and capture probe) per each square micron, and each square micron is observed by an individual pixel of an ultra-sensitive CCD. Next, by adding the digested DNA sample to the pre-formed array surface and ligating with T4 ligase to capture probes, the novel rSBH reaction site is achieved consisting of one target per pixel. The excess sample is removed from the array surface and via heating and additional washing, the dsDNA gives rise to ssDNA. Here, a phosphorylation strategy is employed within the capture probe design to assure only one strand is actually covalently ligated to the rSBH array and the other is removed by the wash.

Localized in situ amplification of targets may be necessary to create satisfactory signals (amplitude and accuracy) for detection adapting well-known techniques (Andreadis and Chrisey, *Nucl. Acids Res.* 28:E5 (2000); Abath et al., *Biotechniques* 33:1210 (2002); Adessi et al., *Nucl. Acids Res.* 28:E87 (2000), all of which are herein incorporated by reference in their entirety). Isothermal strand displacement techniques may be the best suited for localized low copy number amplification. In order to space the capture probe, it is necessary to dope in spacer probes and primer probes. These probes share some conserved sequence and structure and each can function in the role described by their name. Hence, capture probes capture the target DNA, spacer probes help form the properly spaced monolayer of probes, and if necessary, primer probes are present for the in situ amplification. All targets work off the same arrayed primer sequence simplifying the task. Once the sample is ligated to the array, the free termini of the arrayed DNA will get a universal primer for amplification. The in situ amplification is conducted on the molecules within the array using standard protocols and materials (i.e. primers, polymerase, buffer, NTPs, etc.). Only approximately 50 copies are needed, although 10-1000 would suffice. Each target can be amplified with different efficiency without affecting sequence analysis.

In summary, sample integration and rSBH array formation requires DNA digestion of the product from crude sample preparation, isolation, and integration into the substrate to form the rSBH array. The present invention provides for reagents and kits related to each of the digestion, isolation and ligation steps.

7. EXAMPLES

7.1 Sequencing a Bacterial Genome

The entire bacterial genome of a common non-virulent lab strain is sequenced. An *E. coli* strain is chosen that has been well characterized and the sequence is already known. The entire genome is sequenced in a single one-day assay. This assay demonstrates the full operation of the diagnostic system as well as defines the critical specifications related to projecting input and output of the system and universal requirements for crude sample isolation and preparation.

A single colony from a streak plate or a few milliliters of liquid culture provides ample material. Cells are lysed and DNA is isolated using protocols well known in the art (see Sambrook et al, *Molecular Cloning: A Laboratory Manual*, Cold Spring Harbor Laboratory Press, NY (1989) or Ausubel et al., Current Protocols in Molecular Biology, John Wiley & Sons, New York, N.Y. (1989), both of which are herein incorporated by reference in their entirety). The yield is not critical; rather the quality of DNA is the important factor. Sample specifications defined in this example apply to all other samples. For final analysis, a genome copy number of 10-100 copies is used. The additional requirements for this assay are: 1) the DNA is free of DNA processing enzymes; 2) the sample is free of contaminating salts; 3) the entire genome is equally represented and constitutes a majority of the total DNA; 4) the DNA fragments are between 500 and 50,000 bp in length; and 5) the sample is provided as a sterile solution of DNA at a known concentration (for example, 1 µl at 1.0 µg/ml is sufficient).

The input copy number of 10-100 copies assures overlap of the entire genome and tolerates poor capture of targets on the array. With 10-100 copies, enough overlapping fragments are obtained to assure excellent success of base calling and high accuracy. The mass of the rSBH sample is approximately 1-10 pg, the majority of which is used to characterize and quantify the sample. Samples for analysis are obtained by serial dilution of the characterized product.

The DNA must be free of proteins, particularly nucleases, proteases, and other enzymes. Phenol-based extractions, such as PCl, are used to remove and inactivate most proteins (Sambrook et al., 1989, supra; Ausubel et al., 1989, supra). Hypotonic lysis or detergent-based lysis (with nuclease inhibitor cocktails such as EDTA and EGTA) followed by PCl extraction is a rapid and efficient sample digest and DNA isolation in a single step. A phase lock extraction (available through 3'5') simplifies this task and yields clean DNA. No digestion of the DNA is required at this time since sheer forces during lysis and extraction give rise to fragments in the desired range. Remove of phenol is achieved through rigorous cleaning of the DNA (i.e. subsequent chloroform extraction, ethanol precipitation, and size exclusion). Phenol leaves an ultraviolet (UV) spectral signature which is used to test for purity and DNA quantification.

The DNA must be free of contaminating salts and organics and suspended in an SBH compatible Tris buffer. This is achieved by size exclusion chromatography or micro-dialysis.

The crude DNA sample ranges from 500 bp to 50,000 bp. Fragments below 500 bp are difficult to recover in isolation and purification and also affect the arraying process. Fragments larger than 50,000 bp are difficult to dissolve and can irreversibly aggregate.

The sample is provided as a sterile solution of at least 1 µl at 1 µg/ml. The total required amount of crude DNA is only ~1 ng to 1 pg, which is less than 1% of the amount carried over to sequencing.

For the final sample preparation, the DNA is digested to yield fragments of an expected average length of approximately 250 bp harboring sticky ends which are used to array the molecules on the combinatoric array surface. The molecules are spaced such that one molecule is found per square micron, which is observed by a single pixel of a CCD camera and represents a virtual reaction well within an array of millions of wells. This requires elimination of self-assembly monolayer (SAM) effects. An enzyme-driven protocol is used which ligates samples to specific sites that are spaced within a combinatorial array monolayer that is chemically attached to the surface of the detection substrate. The capture array is driven via SAM chemistry, but the small variance in the terminal complementary overhangs should not give rise to islands of like sequence. Thus, the substrate is prepared with the capture array and samples are attached to the substrate surface by enzymatic ligation of appropriate overhangs.

Alternatively, it may be necessary to amplify each target in situ resulting in an "amplicon." The amplification is achieved using a universal primer adaptor that is ligated to the target sequence by the termini that did not get attached in the initial capture ligation. DNA polymerase and NTPs are used to synthesize a new strand and displace the original complement, providing a displaced strand which has complementary elements in the capture array and thus in turn is captured and ligated. It is expected to generate ~10 copies through linear amplification. Alternatively, exponential amplification strategies can be used to yield 100-1000 copies per micron.

The arrayed sample, either single molecule or localized amplicon, is subjected to rSBH cycle sequencing using dedicated probes and integrated microfluidics. Bioinformatics is fully integrated for data collection, storage, analysis and sequence alignment. The result is reported as the genomic sequence of the candidate organism with statistical analysis of base calling and accuracy.

7.2 Sample Preparation from *B. anthracis* and *Y. pestis* Cell Cultures or Blood Samples 7.2.1 Whole Genome Analysis Isolation of a specific pathogen from a crude sample requires isolation or enrichment of the cells from the crude sample followed by lysis to yield the specific genome. Standard biochemistry and cell biology lab techniques, such as fractional centrifugation, filtration, culture, or affinity chromatography, are used to isolate the cells and then extract the genome. Typically, most pathogens are at least two orders of magnitude smaller than human cells and orders of magnitude larger than most bio-molecular structures, thus allowing reasonably facile isolation by traditional physical techniques. It is preferable to employ commercially available antibodies or other affinity tools already available for certain targets, such as viral coat proteins, to streamline isolation and minimize risk. Upon enrichment of the organisms, they are lysed using standard procedures and the DNA is isolated.

Alternatively, genomic amplification can be done using specific primers (for heterogeneous crude samples) harboring reversible affinity tags or a universal set of primers (for isolated cell types). Samples are subjected to lysis and if necessary, crude DNA isolation. Primers are added to the crude sample along with the amplification cocktail and the product is isolated through reversible tagging and affinity capture.

7.2.2 Genomic Footprint Analysis

This method involves amplification of a specific set of footprinting genes specific to the organism of interest. By simultaneously examining multiple genetic regions, different strains of the same pathogen can be distinguished or large numbers of distinct pathogens can be screened. Assays that can be used to detect a variety of biothreat pathogens are described in (Radnedge et al., *App. Env. Micro.* 67:3759-3762 (2001); Wilson et al., *Molecular and Cellular Probes* 16:119-127 (2002); Radnedge et al., *Microbiology* 148:1687-1698 (2002); Radnedge et al., *Appl. Env. Micro*. in press (2003), all of which are herein incorporated by reference in their entirety). Regions of DNA are identified that are specific to the pathogen of interest, but not present in close relatives of the pathogen. Primers are then designed to check for amplification of a DNA product in environmental samples. *B. anthracis* and *Y. pestis* are used as model organisms. Defined quantities of pathogen cells are mixed with human blood to determine the sensitivity of detection. An early-stage symptomatic patient will have $>10^4$ cells/ml blood for either of these pathogens. The goal is to detect the pathogen before it gets to the symptomatic stage. Blood samples are examined that possess from $10^1$ to $10^5$ cells/ml to determine the accuracy of detection. Genomic DNA is extracted using the QiaAmp Tissue Kit 250 (Qiagen, Inc., Valencia, Calif.) or the NucleoSpin Multi-8 blood kit (Macherey-Nagel Inc., Düren, Germany). Pathogen concentration is determined by plating mid-log cells and by microscopic counting with a haemocytometer: 10 μl of diluted cells are added to 190 μl of human blood to approximate pre-symptomatic concentrations. Genomic DNA is then extracted and prepared for amplification of diagnostic targets and genes.

7.3 Assay for Preparation of 100 Diagnostic Targets from Biohazard-Free *B. anthracis* and *Y. pestis* DNA Samples Targets are selected to identify regions of potential antibiotic resistance, mutations in virulence genes and vector sequences suggestive of genetic engineering. Such targets, especially virulence and antibiotic resistance genes, are generally not unique to a specific pathogen but provide additional qualitative information. Targeted DNA will be amplified with 50 primer pairs to interrogate relevant unique and qualitative regions of each pathogen. The products are pooled into one sample for SBH analysis. Multiplex primer pairs can be used to simplify the amplification of target sequences.

Primers are used that have a cleavable tag for isolation of the amplicon from the original complex DNA mixture. Preferably, the tag is biotin/streptavidin-based with a DTT cleavable disulfide bridge or specifically engineered restriction site within the primer. Amplicons are isolated by the affinity tag and released as a purified DNA sample. Products are further purified by size exclusion to remove any unwanted salts and organics and then quantified for downstream integration.

7.4 Sequencing Samples from Microbial Biofilms rSBH in combination with field studies and FISH is used to examine the biofilm community genome. Using rSBH a biofilm community is sequenced at more than one time point and from distinct habitats to determine the number of genospecies. The analysis is facilitated by DNA normalization between samples to highlight differences in the genospecies level of community structure and to provide significant coverage of the genomes of low abundance genospecies. 16S rDNA clone libraries are constructed for each sample according to well-established protocols. FISH probes to distinguish phylotypes and targeted to SNPs to distinguish subtle variants within phylotypes are used to map out patterns of distribution and allow correlation between SBH-defined genospecies and 16S rDNA phylotype distribution. Samples are collected from physically and chemically distinct habitats and key environmental parameters are measured at the time of sample collection, including pH, temperature, ionic strength, redox state (i.e. the $Fe^{2+}/Fe^{3+}$ ratio), and concentration of dissolved organic carbon, copper, zinc, cadmium, arsenic and other ions.

7.5 Base Calling Simulation Test

Simulated data was generated for *E. coli* with 250 bp (average length) fragments overlapped by 90%. The first 10,000 fragments were analyzed using standard single base change calling. This amount was more than sufficient to check for accuracy and timing. The reference lookup successfully found the 10,000 fragment positions in the full 4 Mbp reference genome. Additionally, base calling was correctly performed on each of the fragments. Each fragment was binned against the full 4 Mbp reference, which validated the lookup timing and accuracy, independent of the number of fragments tested. The time required for reference lookup and base calling was 0.8 seconds/fragment. The base calling included testing for single base changes and normalizations used to optimize the accuracy. A margin on either side of the fragment was allowed in the reference lookup, which increased the resolving time.

7.6 Arraying and Imaging Individual Q-Dots

Two microliters of 0, 8, 160 and 400 pM streptavidin-conjugated Qdots (Qdot Inc, Hayward, Calif.) were deposited on the surface (in the center of the coverslip) of biotin-modified coverslips (Xenopore Inc., Hawthorne, N.J.) for 2 min. The droplet was removed via vacuum. 10 µl of DI water was applied and removed in the same manner. This wash was repeated 4 times. The coverslip was placed treated side down on a clean glass slide. 1 µl of water was used to stick the slide to the surface. A small amount of objective immersion oil was placed at the edge of the coverslip to stop evaporation by creating a seal around the coverslip.

The substrate was imaged using a Zeiss axiovert 200 with epi-illumination through a Plan Fluar 100× oil immersion (1.45 na) objective. A standard chroma Cy3 filter set was used to image the 655 nm emission from the Qdots. The transmission spectra for the chroma Cy3 emission filter overlaps with the emission filter for the 655 nm Qdots. Images were recorded using a Roper Scientific CoolSNAP$_{HQ}$™ camera (Roper Scientific, Inc., Tuscon, Ariz.) using a 50 ms exposure time. From the images, it was apparent that higher Qdot concentrations produced more visible spots. Control coverslips spotted with water had only a few visible spots due to various contaminations. In addition to seeing groups of Qdots with steady fluorescence of expected color, individual blinking spots of varying intensity and color were also seen. These features indicated that these small spots were single Qdots. The intensity differences may be explained by far-off wavelength, out of the focus plane, or by variation in activity between individual particles. The significance of these results is that individual molecules, if labeled with Qdots, can be detected with advanced microscopy. Further reduction of background using the TIRF system and more efficient excitation by laser is expected to allow routine accurate detection of single fluorescent molecules.

7.7 Ligation Signals and Spotted Targets and Oligonucleotides

These experiments were designed to demonstrate: 1) spotted target can be used as a template for ligation of two probes with good full-match specificity, 2) spotted oligonucleotides can be used as primers (or to capture probes) for attaching target DNA to the surface.

A. Slide Setup

Four 5'-$NH_2$-modified oligonucleotides (see Table 1 for sequences) that can serve as targets or primers or capture probe were spotted at 7 different concentrations (1, 5, 10, 25, 50, 75, 90 pmole/ul) on a 1,4-phenylene diisothiocyanate derivatized slide, and each concentration was repeated 6 times. The long Tgt2-Tgt1-rc oligonucleotide contains the entire Tgt2 sequence and a portion of a sequence complementary to Tgt1 (underlined portions are complementary in the anti-parallel orientation). Tgt2-Tgt1-rc was used as a test target that can be captured by Tgt1 and the efficacy of capture can be tested by comparing 2-probe ligation to Tgt2 sequence directly spotted and captured by Tgt1.

TABLE 1

Oligonucleotides used as targets or primers or capture probes

| Primer name | Sequence | SEQ ID NO: |
|---|---|---|
| Tgt1 | NH-C6-C18-C18-CCGATCTTAG<u>CAACGCATACAAACGTCAGT</u>-3' (30 mer) | 1 |
| Tgt2 | NH-C6-C18-C18-TTCGACACGTCCAGGAACGTGCTTCAATGA-3' (30 mer) | 2 |
| Tgt3 | NH-C6-C18-C18-GTCAACTGTACCTATTCAGTCACTACTCAT-3' (30 mer) | 3 |
| Tgt4 | NH-C6-C18-C18-CAGCAGTACGATTCATACTTGCATAT-3' (26 mer) | 4 |
| Tgt2-Tgt1-rc | TTCGACACGTCCAGGAACGTGCTTCAATGA<u>ACTGACGTTTGTATGCGTTG</u>-3' | 5 |

B. Experiment 1

Hybridization/Ligation was carried out in a closed chamber at room temperature for 1 hour. The reaction solution contained 50 mM Tris, 0.025 units/µl T4 ligase (Epicentre, Madison, Wis.), and 0.1 mg/ml BSA, 10 mM $MgCl_2$, 1 mM ATP, pH 7.8 and varying amount of ligation probe pools (see, Table 2) from 0.005 to 0.5 pmole/µl. After reaction, the slide was washed by 3×SSPE for 30 minutes at 45° C., then rinsed with dd$H_2O$ 3 times and spun dry. These slides were then scanned at Axon GenePix4000A with PMT setting at 600 mV.

TABLE 2

Ligation probe pools

| Pool 1 | FM-pool | SMM1-pool | SMM2-pool |
|---|---|---|---|
| Tgt1-5'-probe | 5'-NNNTGTATG (SEQ ID NO: 6) | 5'-NNNTGTAAG (SEQ ID NO: 7) | 5'-NNNTGTATG (SEQ ID NO: 6) |
| Tgt1-3'-probe | 5'-CGTTGNN-* (SEQ ID NO: 8) | 5'-CGTTGNN-* (SEQ ID NO: 8) | 5'-CGATGNN-* (SEQ ID NO: 9) |
| Tgt2-5'-probe | 5'-NNNCACGTT (SEQ ID NO: 10) | 5'-NNNCACGAT (SEQ ID NO: 11) | 5'-NNNCACGTT (SEQ ID NO: 10) |
| Tgt2-3'-probe | 5'-CCTGGNN-* (SEQ ID NO: 12) | 5'-CCTGGNN-* (SEQ ID NO: 12) | 5'-CCAGGNN-* (SEQ ID NO: 13) |
| Tgt3-5'-probe | 5'-NNNGACTGA (SEQ ID NO: 14) | 5'-NNNGACTCA (SEQ ID NO: 15) | 5'-NNNGACTGA (SEQ ID NO: 14) |
| Tgt3-3'-probe | 5'-ATAGGNN-* (SEQ ID NO: 16) | 5'-ATAGGNN-* (SEQ ID NO: 16) | 5'-ATCGGNN-* (SEQ ID NO: 17) |
| Tgt4-5'-probe | 5'-NNNGTATGA (SEQ ID NO: 18) | 5'-NNNGTATCA (SEQ ID NO: 19) | 5'-NNNGTATGA (SEQ ID NO: 18) |
| Tgt4-3'-probe | 5'-ATCGTNN-* (SEQ ID NO: 20) | 5'-ATCGTNN-* (SEQ ID NO: 20) | 5'-ATGGTNN-* (SEQ ID NO: 21) |

Note:
*indicates Tamra labeled, the underlined base indicates the position of single mismatch.

C. Experiment 2

A slide spotted with four NH$_2$-modified 26-30-mers was hybridized with 1 pmole of long target Tgt2-Tgt1-rc (Table 1) in 20 μl of 50 mM Tris, and 0.1 mg/ml BSA, 10 mM MgCl$_2$, pH 7.8 at room temperature for 2 hour. The slide was washed with 6×SSPE at 45° C. for 30 minutes, and then incubated with ligation probes (Tgt2-5'-probe and Tgt2-3'-probe, Table 2) at room temperature for 1 hour in the presence of 0.5 Unit/20 μl of T4 ligase. After the reaction, slide was washed and scanned as described above.

D. Results

1. Ligation Signal Depends on the Concentration of Spotted Targets and the Concentrations of the 5'Probe and 3'Probe in the Reaction Solution.

FIG. 12 shows the ligation signal dependence on spotted targets and ligation probes in the solution. The highest signal was achieved when spotted target concentration was approximately 75 pmole/μl, and ligation probes (probe-5' and probe-3') were approximately 1 pmole in 20 μl of reaction solution. These dependencies indicate that the observed signals were actually ligation-depend signals and spotted target can be used as a template for ligation. Discrimination between full match ligation probe and single mismatch probe was about 4-20 fold (Table 3).

TABLE 3

Full match and single mismatch discrimination of ligation signal

| Target | FM/SMM of 5'-probe | FM/SMM of 3'-probe |
|---|---|---|
| Tgt1 | 14 | 20 |
| Tgt2 | 7 | 12 |
| Tgt3 | 9 | 16 |
| Tgt4 | 4 | 4 |

2. Spotted Oligonucleotides can be Used as a Primer (or Capture Probe) to Efficiently Attach Target DNA.

Oligonucleotide 1 (Tgt1) spotted on the slide served as a capture probe for target Tgt2-Tgt1-rc, which comprises a section of reverse complement sequence of Tgt1 at its 3'-side, and a Tgt2 sequence at its 5'-side. After hybridization/capture of Tgt2-Tgt1-rc, the ligation probes (Tgt2-5'-probe and Tgt2-3'-probe) were hybridized/ligated on the dots of the Tgt2 target as well on the dots with the Tgt1 target. The observed ligation signals are shown in FIG. 13. Clearly, at this condition, spotted target can be used as a primer (or capture probe) to attach target DNA in the form available for hybridization/ligation of short probes used for sequence determination.

I claim:

1. A method for determining all or part of the sequence of a plurality of target nucleic acid sequences comprising:
   (a) providing an array comprising a plurality of different target nucleic acid sequences randomly distributed on a surface of said array, wherein each target nucleic acid comprises a first target domain and an adjacent second target domain, wherein said first and second target domains each comprise multiple nucleotides;
   (b) contacting said array with:
      (i) a first probe set comprising:
         1. a first probe pool comprising probes complementary to said first target domains;
         2. a second probe pool comprising probes complementary to said second target domains;
   wherein at least one of said first and second probe pools comprises a label;
   (c) ligating probes from said first probe pool and probes from said second probe pool when hybridized to said first and second target domains to form first ligated probes;
   (d) detecting said first ligated probes to determine at least one nucleotide of said first target domain;
   (e) removing said first ligated probes;
   (f) repeating steps (b)-(d) to determine all nucleotides of said first target domain, wherein each nucleotide of said first target domain is determined multiple times.

2. A method according to claim 1 wherein said label is selected from the group consisting of fluorophores, radioisotopes, chromophores, and chemiluminescent moieties.

3. A method according to claim 1 wherein each of said first and second probe pools comprises a label.

4. A method according to claim 3 wherein the label on said first probe pool and the label on said second probe pool are FRET pairs.

5. A method according to claim 3, wherein said label is attached to the terminus of each of said first and second probe pools.

6. A method according to claim 5, wherein said probes of said first probe pool have free 3' hydroxyl groups and wherein said probes of said second probe pool have free 5' phosphate groups.

7. A method according to claim 1, wherein said plurality of target nucleic acid sequences comprise genomic DNA.

8. A method according to claim 1, wherein said first and second probe pools comprise probes of 8 to 10 bases in length.

9. A method according to claim 1, wherein said plurality of target nucleic acids comprises at least about 100, 1000, 10,000, 100,000, 1 million, or 10 million target nucleic acids.

10. A method according to claim 1, wherein said plurality of target nucleic acids are treated with a phosphatase such that said target nucleic acids are unable to ligate to each other.

11. A method according to claim 1, wherein said plurality of target nucleic acids are prepared so that they cannot be ligated to each other through amplification with random primers that have no phosphate at their 5' ends.

12. A method according to claim 1, wherein said plurality of target nucleic acids is immobilized to said surface.

13. A method according to claim 12, wherein said plurality of target nucleic acids is immobilized to said surface at a density of a single target nucleic acid per pixel.

14. A method according to claim 12, wherein said plurality of target nucleic acids is immobilized to said surface by a member selected from: passive adsorption, UV light, covalent binding, and formation of an amide bond between said target nucleic acids and said surface.

15. A method according to claim 12, wherein said plurality of target nucleic acids is immobilized to said surface through a reactive group, wherein said reactive group is a member selected from a hydroxyl group, a carboxyl group, and an amino group.

16. A method according to claim 12, wherein each of said plurality of target nucleic acids comprises an adapter, wherein said surface comprises capture oligonucleotides, and wherein said plurality of target nucleic acids are immobilized to said surface through hybridization of said adapters to said capture oligonucleotides.

17. A method according to claim 1, wherein probes within the same pool cannot ligate to each other.

18. A method according to claim 1, wherein said label is attached to said at least one of said first and second probe pools using a method that is a member selected from: direct chemical labeling, kinasing and nick-translation.

19. A method according to claim 1, wherein prior to said detecting step (d), unligated probes are removed from said array.

20. A method according to claim 1, wherein at least one of said first and second probe pools is a universal probe pool comprising probes of 10 bases in length.

21. A method according to claim 1, wherein prior to said contacting step (b), said target nucleic acid sequences undergo in situ amplification.

22. A method according to claim 21, wherein said target nucleic acid sequences are amplified at least 10-, 100-, 1000-, or 10,000-fold.

23. A method according to claim 1, wherein all of said probes in said first probe pool comprise an identical sequence.

24. A method according to claim 1, wherein said plurality of target nucleic acids comprises one or more genomes.

25. A method according to claim 1, wherein said plurality of target nucleic acids comprises a member selected from entire genes, mixtures of genes, mixtures of mRNAs, segments of chromosomes, entire chromosomes, and mixtures of chromosomes.

26. A method for determining all or part of the sequence of a plurality of target nucleic acid sequences comprising:
  (a) providing an array comprising a plurality of different target nucleic acid sequences randomly distributed on a surface of said array, wherein each target nucleic acid comprises a first target domain and an adjacent second target domain, wherein said first and second target domains each comprise multiple nucleotides;
  (b) contacting said array with:
    (i) a first probe set comprising:
      1. a first probe pool comprising probes complementary to said first target domains;
      2. a second probe pool comprising probes complementary to said second target domains;
  wherein at least one of said first and second probe pools comprises a label;
  (c) ligating probes from said first probe pool and probes from said second probe pool when hybridized to said first and second target domains to form first ligated probes;
  (d) detecting said first ligated probes to determine at least one nucleotide of said first target domain;
  (e) removing said first ligated probes;
  (f) contacting said array with:
    (i) a second probe set comprising:
      1. a third probe pool comprising probes complementary to said first target domains;
      2. a fourth probe pool comprising probes complementary to said second target domains;
  wherein at least one of said third and fourth probe pools comprises a label;
  (g) ligating probes from said third probe pool and probes from said fourth probe pool when hybridized to said first and second target domains to form second ligated probes;
  (h) detecting said second ligated probes to determine at least one nucleotide of said first target domain,
wherein at least one nucleotide of said first target domain is determined by both said detecting of said first ligated probes and said detecting of said second ligated probes.

* * * * *